US012559457B2

(12) United States Patent
Gray et al.

(10) Patent No.: US 12,559,457 B2
(45) Date of Patent: Feb. 24, 2026

(54) SULFONAMIDE DERIVATIVES FOR PROTEIN DEGRADATION

(71) Applicant: DANA-FARBER CANCER INSTITUTE, INC., Boston, MA (US)

(72) Inventors: Nathanael S. Gray, Boston, MA (US); Eric Fischer, Chestnut Hill, MA (US); Hojong Yoon, Cambridge, MA (US); Tinghu Zhang, Brookline, MA (US); Tyler Faust, Brookline, MA (US); Katherine Donovan, Boston, MA (US); Quan Cai, Shanghai (CN); Zhengnian Li, Newton, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 18/375,003

(22) Filed: Sep. 29, 2023

(65) Prior Publication Data

US 2024/0083847 A1 Mar. 14, 2024

Related U.S. Application Data

(62) Division of application No. 16/767,822, filed as application No. PCT/US2019/014919 on Jan. 24, 2019, now Pat. No. 11,807,606.

(60) Provisional application No. 62/621,915, filed on Jan. 25, 2018.

(51) Int. Cl.

| | |
|---|---|
| ***C07D 209/08*** | (2006.01) |
| ***C07D 231/56*** | (2006.01) |
| ***C07D 401/12*** | (2006.01) |
| ***C07D 403/12*** | (2006.01) |
| ***C07D 471/04*** | (2006.01) |
| ***C07D 487/04*** | (2006.01) |

(52) U.S. Cl.
CPC ......... *C07D 209/08* (2013.01); *C07D 231/56* (2013.01); *C07D 401/12* (2013.01); *C07D 403/12* (2013.01); *C07D 471/04* (2013.01); *C07D 487/04* (2013.01)

(58) Field of Classification Search
CPC ............................ C07D 231/56; C07D 209/08
See application file for complete search history.

(56) References Cited

U.S. PATENT DOCUMENTS

| | | | |
|---|---|---|---|
| 5,721,246 | A | 2/1998 | Yoshino et al. |
| 6,673,787 | B2 | 1/2004 | Haneda et al. |
| 2009/0047278 | A1 | 2/2009 | Owa et al. |
| 2010/0267754 | A1 | 10/2010 | Wakabayashi et al. |
| 2017/0065719 | A1 | 3/2017 | Qian et al. |
| 2017/0334932 | A1 | 11/2017 | Chan et al. |
| 2020/0290964 | A1 | 9/2020 | Gray et al. |
| 2021/0002295 | A1 | 1/2021 | Gray et al. |

FOREIGN PATENT DOCUMENTS

| | | | |
|---|---|---|---|
| WO | 2019118851 | A1 | 6/2019 |
| WO | 2019147783 | A1 | 8/2019 |

OTHER PUBLICATIONS

Registry No. 1241179-33-8, entered in STN on Sep. 15, 2010; found in Chemical Library in CHEMCATS.*
Registry No. 1241124-96-8, entered in STN on Sep. 15, 2010; found in Chemical Library in CHEMCATS.*
Registry No. 1340897-91-7; entered in STN on Nov. 4, 2011; Chemical Library: Supplier: ChemDiv, Inc.*
Farnaby et al., "BAF complex vulnerabilities in cancer demonstrated via structure-based PROTAC design," Nature Chemical Biology 15:672-680 (2019).
Golub et al., "Molecular Classification of Cancer: Class Discovery and Class Prediction by Gene Expression Monitoring," Science 286(5439):531-537 (1999).
Lala et al., "Role of nitric oxide in tumor progression: Lessons from experimental tumors," Cancer and Metastasis Reviews 17(1):91-106 (1998).
Medline Plus, "Cancer," [online], Retrieved from the internet, URL: http://www.nlm.nih.gov/medlineplus/cancer.html, 10 pages.
CAPLUS—Accession No. 2016:2049178 from U.S. Pat. No. 8,906,896 (Bierbach) Dec. 9, 2014 (abstract) STN [database online].
CAPLUS—Accession No. 2011:1200919 from EP2366687A2 (Chern et al.) Sep. 21, 2011 (abstract) STN [database online].
CAPLUS—Accession No. 2003:221507 from WO2003022271A1 (Hanada et al.) Mar. 20, 2003 (abstract) STN [database online].
CAPLUS—Accession No. 1997:326877 from WO9712860A1 (Kamiya et al.) May 23, 1997 (abstract) STN [database online].
CAPLUS—Accession No. 1994:270013 from Murakami et al. Chemical & Pharmaceutical Bulletin 1993 (abstract) STN [database online].
CAPLUS—Accession No. 2002:439077 from JP2002167376A (Nagai et al.) Jun. 11, 2002 (abstract) STN [database online].
CAPLUS—Accession No. 2004:902219 from WO2004091664A1 (Owa et al.) Oct. 28, 2004 (abstract) STN [database online].
CAPLUS—Accession No. 2006:1217188 from Owa, T. Yuki Gosei Kagaku Kyokaishi 2006 (abstract) STN [database online].
CAPLUS—Accession No. 2011:750870 from WO2011072174A1 (Salituro et al.) Jun. 16, 2011 (abstract) STN [database online].
CAPLUS—Accession No. 2007:410811 from WO2007040166A1 (Sone et al.) Apr. 12, 2007 (abstract) STN [database online].
CAPLUS—Accession No. 2017:684678 from Uehara et al. Nature Chemical Biology 2017 (abstract) STN [database online].
CAPLUS—Accession No. 1949:2625 from Arnold et al. Journal of the American Chemical Society 1948 (abstract) STN [database online].

(Continued)

*Primary Examiner* — Shawquia Jackson
(74) *Attorney, Agent, or Firm* — ArentFox Schiff LLP; Daniel W. Clarke; Shawn P. Foley

(57) ABSTRACT

DCAF15 is a substrate recognition (adaptor) protein of E3 ubiquitin ligase. Disclosed herein are compounds that recruit ubiquitin ligase $CRL4^{DCAF15}$, to a target RNA recognition motif (RRM), causing its degradation. Also disclosed herein are compositions and methods of use in treating associated disorders and diseases.

16 Claims, 1 Drawing Sheet

(56) References Cited

OTHER PUBLICATIONS

Pubchem CID 22727470, pp. 1-13, Create Date: Dec. 5, 2007; p. 4.
Pubchem CID 25044530, pp. 1-13, Create Date: Nov. 17, 2008; p. 4.
International Search Report and Written Opinion for International Application No. PCT/US18/65701 mailed Feb. 21, 2019, 23 pages.
International Search Report and Written Opinion for International Application No. PCT/US19/14919 dated Mar. 22, 2019, 18 pages.

* cited by examiner

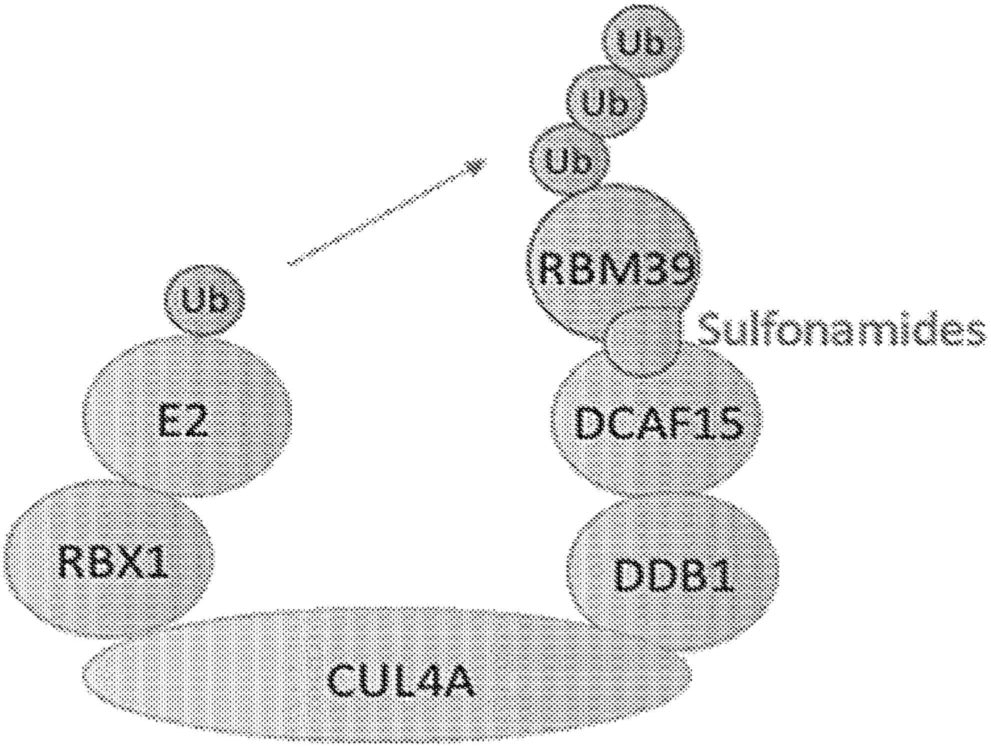
Ub
Ub
Ub
RBM39
Sulfonamides
Ub
E2
DCAF15
RBX1
DDB1
CUL4A

SULFONAMIDE DERIVATIVES FOR PROTEIN DEGRADATION

RELATED APPLICATIONS

This application is a U.S. Divisional Application of U.S. application Ser. No. 16/767,822, filed May 28, 2020, which is a national stage application, filed under 35 U.S.C. § 371, of International Application No. PCT/US2019/014919, filed Jan. 24, 2019, which claims the benefit of priority under 35 U.S.C. § 119(e) to U.S. Provisional Application No: 62/621,915, filed on Jan. 25, 2018, each of which is incorporated herein by reference in its entirety.

BACKGROUND

Targeted protein degradation is an emerging strategy to eliminate the function of a protein of interest. To date this process has been accomplished using ligands that can bind and recruit the ligase activity of CRBN, VHL, MDM2 and IAP proteins (Uehara et al., Nature Chemical Biology, 13, 675-680).

DDB1- and CUL4-associated factor 15 (DCAF15) is a ubiquitin ligase component of $CRL4^{DCAF15}$. DCAF15 is a substrate recognition (adaptor) protein of E3 ubiquitin ligase that regulates cell proliferation, cell survival, DNA repair, and genomic integrity through targeted degradation via ubiquitination of key regulators. Targeted degradation of select proteins utilizing DCAF15 is attractive as it combines the benefits of small molecule inhibitors without the associated drawbacks such as off-target effects or toxicity.

Aryl sulfonamides, such as indisulam, are known to facilitate the degradation of RNA recognition motifs (RRMs) through the recruitment of DCAF15 (Han et al. Science, 1-3, March 2017). RNA splicing in cancer cells controls the expression of numerous oncoproteins or tumor suppressors. In turn, this RNA splicing is under the control of specific RRMs, such as RMM39. Unregulated expression of RMM39 has been implicated in lymphoid and hematopoietic cancers such as chronic lymphocytic leukemia or acute myeloid leukemia (Moore et al. Science, 309, 1514-1518, September 2005). Provided herein are compounds that selectively target RNA splicing in cancer through the targeted degradation of RMMs, with lessened adverse reactions when compared to previous treatments, e.g., spliceostatin.

SUMMARY

Disclosed herein are compounds of Formula (I):

Formula (I)

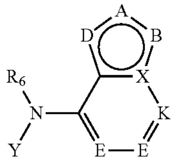

or a pharmaceutically acceptable salt or stereoisomer thereof, wherein:

A is $CR_2$ or N;

B is $CR_3$ or N;

X is C or N;

D is $CR_{1A}$ or $NR_{1B}$;

K is $CR_4$ or N;

each E is independently $CR_5$ or N;

Y is

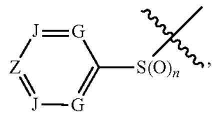, $-SO_2$ alkyl, or $-C(O)$alkyl;

each G is independently $CR_7$ or N;

each J is independently $CR_8$ or N;

Z is $CR_9$ or N;

$R_{1A}$ is hydrogen, halo, CN or alkyl;

$R_{1B}$ is hydrogen or alkyl;

$R_2$ is hydrogen, alkyl, halo, $-OH$, $-CO_2R_{10}$), $-CN$, or $-NO_2$;

$R_3$ is hydrogen, halo, alkyl, $-NO_2$, $-OH$, $-CN$, $-CHO$, $-CO_2R_{10}$, $-C(O)N(R_{11})_2$, or $-SO_2N(R_{11})_2$;

$R_4$ is hydrogen, alkyl, halo, aryl, $-CN$, $-NO_2$, $-N(R_{11})_2$, $-CHO$, $-CO_2R_{10}$, $-C(O)N(R_{11})_2$, $-SO_2N(R_{11})_2$, or $-OR_{12}$, each $R_5$ is independently hydrogen, halo, alkyl, aryl, $-CN$, $-NO_2$, $-N(R_{13})_2$, $-CHO$, $-CO_2R_{10}$, $-C(O)N(R_{11})_2$, or $-SO_2N(R_{11})_2$;

$R_6$ is hydrogen or alkyl;

each $R_7$ is independently hydrogen, halo, alkyl, $-CN$, $-NO_2$, $-N(R_{13})_2$, $-OR_{12}$, $-CHO$, $-CO_2R_{10}$, $-C(O)N(R_{11})_2$, or $-SO_2N(R_{11})_2$;

each $R_8$ is independently hydrogen, halo, alkyl, $-CN$, $-NO_2$, $-N(R_{13})_2$, $-CHO$, $-CO_2R_{10}$, $-C(O)N(R_{11})_2$, or $-SO_2N(R_{11})_2$;

$R_9$ is hydrogen, halo, alkyl, $-CN$, $-NO_2$, $-N(R_{13})_2$, $-CHO$, $-CO_2R_{10}$, $-C(O)N(R_{11})_2$, aryl, $-OR_{12}$, $-(CH_2)_mN(R_{11})_2$, $-(CH_2)_mN(R_{11})C(O)C_1$-$C_6$ alkyl, $-N(R_{11})C(O)C_1$-$C_6$ alkyl, $-N(R_{11})C(O)$aryl, $-N(R_{11})C(O)N(R_{11})C_1$-$C_6$ alkyl or $-N(R_{11})C(O)N(R_{11})$aryl;

each $R_{10}$ and $R_{11}$ is independently hydrogen or alkyl;

each $R_{12}$ and $R_{13}$ is independently hydrogen, alkyl or aryl;

m is 1, 2, 3, 4, 5 or 6; and n is 1 or 2;

provided that:

a) if $R_8$ is halo or $-CN$, then $R_4$ is not alkyl or $-OR_{12}$;

b) if $R_9$ is $-NO_2$ or $-N(R_{11})_2$, then $R_4$ is not alkyl, halo or $-CN$;

c) if $R_9$ is $-N(R_{11})C(O)C_1$-$C_6$ alkyl, then $R_4$ is not alkyl;

d) if $R_9$ is halo then each J is N; and e) if $R_9$ is $-CN$ then $R_2$ is not hydrogen.

Disclosed herein are compounds of Formula (II):

II

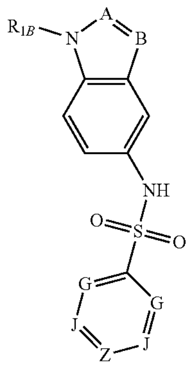

or a pharmaceutically acceptable salt or stereoisomer thereof, wherein:

A is $CR_2$ or N;

B is $CR_3$ or N;

each G is independently $CR_7$ or N;

each J is independently $CR_8$ or N;

Z is $CR_9$ or N;

$R_{1B}$ is hydrogen or alkyl;

$R_2$ is hydrogen, alkyl, or $—CO_2R_{10}$;

$R_3$ is hydrogen, alkyl, or —CN;

each $R_7$ is independently hydrogen, halo, alkyl, —CN, $—NO_2$, $—N(R_{13})_2$, or $—OR_{12}$;

each $R_8$ is independently hydrogen, halo, alkyl, —CN, $—NO_2$, $—N(R_{13})_2$, or $—OR_{12}$;

$R_9$ is hydrogen, halo, alkyl, —CN, $—NO_2$, $—N(R_{13})_2$, or $—OR_{12}$;

each $R_{10}$ and $R_{11}$ is independently hydrogen or alkyl; and each $R_{12}$ and $R_{13}$ is independently hydrogen, alkyl or aryl.

In certain embodiments, disclosed herein are compounds of Formula (I) or Formula (II) that act as degraders of RRM proteins. These compounds are therapeutic agents for the treatment of diseases such as cancer and metastasis, and other RRM protein mediated diseases.

In certain embodiments, disclosed herein are pharmaceutical compositions comprising a compound of Formula (I), Formula (II), or a pharmaceutically acceptable salt thereof, and a pharmaceutically acceptable carrier.

In certain embodiments, disclosed herein are methods of treating or preventing a disease or disorder associated with degradation of a RRM protein, comprising administering to a subject in need thereof a compound of Formula (I), Formula (II), or a pharmaceutically acceptable salt thereof.

In certain embodiments, disclosed herein are methods of treating a disease or disorder associated with degradation of a RRM protein, comprising administering to a subject a compound of Formula (I), Formula (II), or a pharmaceutically acceptable salt thereof.

In certain embodiments, disclosed herein are methods of treating or preventing cancer, comprising administering to a subject a compound of Formula (I), Formula (II), or a pharmaceutically acceptable salt thereof.

In certain embodiments, disclosed herein are compounds of Formula (I), Formula (II), or a pharmaceutically acceptable salt thereof, for use in treating a disease associated with degradation of a RRM protein.

In certain embodiments, disclosed herein is the use of a compound of Formula (I), Formula (II), or a pharmaceutically acceptable salt thereof, in the manufacture of a medicament for the treatment of a disease associated with degradation of a RRM protein.

BRIEF DESCRIPTION OF THE FIGURES

FIG. 1 depicts the recruitment of RBM39 to the CUL4-DCAF15 E3 ubiquitin ligase and polyubiquitination. The polyubiquitination causes subsequent proteasomal degradation of the RBM39 protein.

DETAILED DESCRIPTION

Disclosed herein are compounds of Formula (I):

Formula (I)

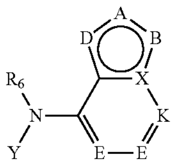

or a pharmaceutically acceptable salt or stereoisomer thereof, wherein:

A is $CR_2$ or N;

B is $CR_3$ or N;

X is C or N;

D is $CR_{1A}$ or $NR_{1B}$;

K is $CR_4$ or N;

each E is independently $CR_5$ or N;

Y is

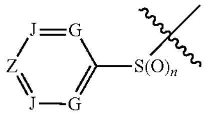 , $—SO_2$ alkyl, or —C(O)alkyl;

each G is independently $CR_7$ or N;

each J is independently $CR_8$ or N;

Z is $CR_9$ or N;

$R_{1A}$ is hydrogen, halo, CN or alkyl;

$R_{1B}$ is hydrogen or alkyl;

$R_2$ is hydrogen, alkyl, halo, —OH, $—CO_2R_{10}$, —CN, or $—NO_2$;

$R_3$ is hydrogen, halo, alkyl, $—NO_2$, —OH, —CN, —CHO, $—CO_2R_{10}$, $—C(O)N(R_{11})_2$, or $—SO_2N(R_{11})_2$;

$R_4$ is hydrogen, alkyl, halo, aryl, —CN, $—NO_2$, $—N(R_{11})_2$, —CHO, $—CO_2R_{10}$, $—C(O)N(R_{11})_2$, $—SO_2N(R_{11})_2$, or $—OR_{12}$, each $R_5$ is independently hydrogen, halo, alkyl, aryl, —CN, $—NO_2$, $—N(R_{13})_2$, —CHO, $—CO_2R_{10}$, $—C(O)N(R_{11})_2$, or $—SO_2N(R_{11})_2$;

$R_6$ is hydrogen or alkyl;

each $R_7$ is independently hydrogen, halo, alkyl, —CN, $—NO_2$, $—N(R_{13})_2$, $—OR_{12}$, —CHO, $—CO_2R_{10}$, $—C(O)N(R_{11})_2$, or $—SO_2N(R_{11})_2$;

each $R_8$ is independently hydrogen, halo, alkyl, —CN, $—NO_2$, $—N(R_{13})_2$, —CHO, $—CO_2R_{10}$, $—C(O)N(R_{11})_2$, or $—SO_2N(R_{11})_2$;

$R_9$ is hydrogen, halo, alkyl, —CN, $—NO_2$, $—N(R_{13})_2$, —CHO, $—CO_2R_{10}$, $—C(O)N(R_{11})_2$, aryl, $—OR_{12}$, —$(CH_2)_mN(R_{11})_2$, —$(CH_2)_mN(R_{11})C(O)C_1$-$C_6$ alkyl, —$N(R_{11})C(O)C_1$-$C_6$ alkyl, —$N(R_{11})C(O)$aryl, —$N(R_{11})C(O)N(R_{11})C_1$-$C_6$ alkyl or —$N(R_{11})C(O)N(R_{11})$aryl;

each $R_{10}$ and $R_{11}$ is independently hydrogen or alkyl;

each $R_{12}$ and $R_{13}$ is independently hydrogen, alkyl or aryl;

m is 1, 2, 3, 4, 5 or 6; and n is 1 or 2;

provided that:

a) if $R_8$ is halo or —CN, then $R_4$ is not alkyl or —$OR_{12}$;

b) if $R_9$ is —$NO_2$ or —$N(R_{11})_2$, then $R_4$ is not alkyl, halo or —CN;

c) if $R_9$ is —$N(R_{11})C(O)C_1$-$C_6$ alkyl, then $R_4$ is not alkyl;

d) if $R_9$ is halo then each J is N; and e) if $R_9$ is —CN then $R_2$ is not hydrogen.

In certain embodiments, the compound of Formula (I) is a compound of Formula (Ia):

Formula (Ia)

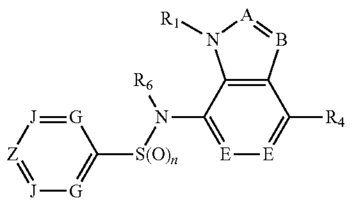

or a pharmaceutically acceptable salt or stereoisomer thereof, wherein:

A is $CR_2$ or N;

B is $CR_3$ or N;

each E is independently $CR_5$ or N;

each G is independently $CR_7$ or N;

each J is independently $CR_8$ or N;

Z is $CR_9$ or N;

$R_1$ is hydrogen or alkyl;

$R_2$ is hydrogen, alkyl, halo, —CN, —$NO_2$;

$R_3$ is hydrogen, alkyl, —$NO_2$, —CN, —CHO, —$CO_2R_{10}$, —$C(O)N(R_{11})_2$, or —$SO_2N(R_{11})_2$;

$R_4$ is alkyl, halo, —CN, —$NO_2$, —$N(R_{11})_2$, —CHO, —$CO_2R_{10}$, —$C(O)N(R_{11})_2$, —$SO_2N(R_{11})_2$, or —$OR_{12}$;

each $R_5$ is independently hydrogen, halo, alkyl, —CN, —$NO_2$, —$N(R_{13})_2$, —CHO, —$CO_2R_{10}$, —$C(O)N(R_{11})_2$, or —$SO_2N(R_{11})_2$;

$R_6$ is hydrogen or alkyl;

each $R_7$ is independently hydrogen, halo, alkyl, —CN, —$NO_2$, —$N(R_{13})_2$, —CHO, —$CO_2R_{10}$, —$C(O)N(R_{11})_2$, or —$SO_2N(R_{11})_2$;

each $R_8$ is independently hydrogen, halo, alkyl, —CN, —$NO_2$, —$N(R_{13})_2$, —CHO, —$CO_2R_{10}$, —$C(O)N(R_{11})_2$, or —$SO_2N(R_{11})_2$;

$R_9$ is hydrogen, halo, alkyl, —CN, —$NO_2$, —$N(R_{13})_2$, —CHO, —$CO_2R_{10}$, —$C(O)N(R_{11})_2$, aryl, —$OR_{12}$, —$(CH_2)_mN(R_{11})_2$, —$(CH_2)_mN(R_{11})C(O)C_1$-$C_6$ alkyl, —$N(R_{11})C(O)C_1$-$C_6$ alkyl, —$N(R_{11})C(O)$aryl, —$N(R_{11})C(O)N(R_{11})C_1$-$C_6$ alkyl or —$N(R_{11})C(O)N(R_{11})$aryl;

each $R_{10}$ and $R_{11}$ is independently hydrogen or alkyl;

each $R_{12}$ and $R_{13}$ is independently hydrogen, alkyl or aryl;

m is 1, 2, 3, 4, 5 or 6; and n is 1 or 2;

provided that:

a) if $R_8$ is halo or —CN, then $R_4$ is not alkyl or —$OR_{12}$;

b) if $R_9$ is —$NO_2$ or —$N(R_{11})_2$, then $R_4$ is not alkyl, halo or —CN;

c) if $R_9$ is —$N(R_{11})C(O)C_1$-$C_6$ alkyl, then $R_4$ is not alkyl;

d) if $R_9$ is halo then each J is N; and e) if $R_9$ is —CN then $R_2$ is not hydrogen.

Disclosed herein are compounds of Formula (II):

Formula (II)

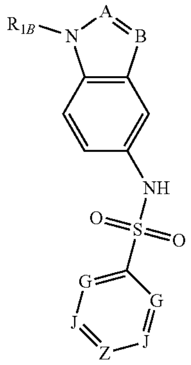

or a pharmaceutically acceptable salt or stereoisomer thereof, wherein:

A is $CR_2$ or N;

B is $CR_3$ or N;

each G is independently $CR_7$ or N;

each J is independently $CR_8$ or N;

Z is $CR_9$ or N;

$R_{1B}$ is hydrogen or alkyl;

$R_2$ is hydrogen, alkyl, or —$CO_2R_{10}$;

$R_3$ is hydrogen, alkyl, or —CN;

each $R_7$ is independently hydrogen, halo, alkyl, —CN, —$NO_2$, —$N(R_{13})_2$, or —$OR_{12}$;

each $R_8$ is independently hydrogen, halo, alkyl, —CN, —$NO_2$, —$N(R_{13})_2$, or —$OR_{12}$;

$R_9$ is hydrogen, halo, alkyl, —CN, —$NO_2$, —$N(R_{13})_2$, or —$OR_{12}$;

each $R_{10}$ and $RH_{11}$ is independently hydrogen or alkyl; and each $R_{12}$ and $R_{13}$ is independently hydrogen, alkyl or aryl.

In certain embodiments, A is $CR_2$. In certain embodiments, B is $CR_3$. In certain embodiments, each E is $CR_5$. In certain embodiments, each G is $CR_7$. In certain embodiments, each J is $CR_8$. In certain embodiments, each J is N. In certain embodiments, Z is $CR_9$. In some embodiments, Z is N. In certain embodiments, K is $CR_4$. In certain embodiments, X is C, while in other embodiments, X is N. In some embodiments, D is CR1A, while in other embodiments, D is $NR_{1B}$. In certain embodiments, Y is

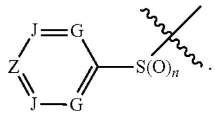

In certain embodiments, Y is —$SO_2$ alkyl, or —C(O)alkyl.

In certain embodiments, $R_{1A}$ is hydrogen. In certain embodiments, $R_{1B}$ is hydrogen. In certain embodiments, $R_2$ is hydrogen. In certain embodiments, $R_2$ is —OH. In certain embodiments, $R_2$ is —$CO_2$ alkyl.

In some embodiments, $R_3$ is hydrogen, halo, —CHO, —OH, —CN, or —$C(O)N(R_{11})_2$. In certain embodiments, $R_3$ is hydrogen. In certain embodiments, $R_3$ is —CHO. In certain embodiments, $R_3$ is —CN.

In certain embodiments, $R_3$ is —C(O)N($R_{11}$)$_2$ and at least one $R_{11}$ is alkyl.

In some embodiments, $R_4$ is hydrogen, halo, aryl, alkyl, —$OR_{12}$, —C(O)N($R_{11}$)$_2$ or —N($R_{13}$)$_2$. In certain embodiments, $R_4$ is hydrogen. In certain embodiments, $R_4$ is halo. In certain embodiments, $R_4$ is alkyl. In certain embodiments, $R_4$ is —$OR_{12}$ and $R_{12}$ is alkyl. In certain embodiments, $R_4$ is —C(O)N($R_{11}$)$_2$ and at least one $R_{11}$ is alkyl. In certain embodiments, $R_4$ is —N($R_{13}$)$_2$ and at least one $R_{13}$ is alkyl.

In some embodiments, $R_5$ is hydrogen. In some embodiments, $R_6$ is hydrogen. In some embodiments, at least one $R_7$ is hydrogen, halo, —$NO_2$ or —$OR_{12}$. In certain embodiments, at least one $R_7$ is hydrogen. In certain embodiments, at least one $R_7$ is halo. In certain embodiments, at least one $R_7$ is —$NO_2$. In certain embodiments, at least one $R_7$ is —$OR_{12}$.

In some embodiments, $R_8$ is hydrogen, alkyl, —CN, —$NO_2$, —N($R_{13}$)$_2$, C(O)N($R_{11}$)$_2$, or —$CO_2R_{10}$. In certain embodiments, at least one $R_8$ is hydrogen. In certain embodiments, at least one $R_8$ is alkyl. In certain embodiments, at least one $R_8$ is —CN. In certain embodiments, at least one $R_8$ is —$NO_2$. In certain embodiments, at least one $R_8$ is —$NH_2$. In certain embodiments, at least one $R_8$ is —C(O)N($R_{11}$)$_2$ and at least one $R_{11}$ is alkyl. In certain embodiments, at least one $R_8$ is —$CO_2R_{10}$ and $R_{10}$ is alkyl.

In some embodiments, $R_9$ is hydrogen, alkyl, halo, —CN, —$NO_2$, —N($R_{13}$)$_2$, —C(O)N($R_{11}$)$_2$, —$CO_2R_{10}$, —$OR_{12}$, —($CH_2$)$_m$N($R_{11}$)$_2$, —($CH_2$)$_m$N($R_{11}$)C(O)$C_1$-$C_6$ alkyl, —N($R_{11}$)C(O)$C_1$-$C_6$ alkyl, —N($R_{11}$)C(O)aryl, or —N($R_{11}$)C(O)N($R_{11}$)aryl. In certain embodiments, $R_9$ is hydrogen. In certain embodiments, $R_9$ is alkyl. In certain embodiments, $R_9$ is halo. In certain embodiments, $R_9$ is —CN. In certain embodiments, $R_9$ is —$NO_2$. In certain embodiments, $R_9$ is alkyl. In certain embodiments, —$CO_2R_{10}$ and $R_{10}$ is alkyl. In certain embodiments, $R_9$ is —$NH_2$. In certain embodiments, $R_9$ is —N($R_{13}$)$_2$ and at least one $R_{13}$ is aryl. In certain embodiments, $R_9$ is —$OR_{12}$ and each $R_{12}$ is hydrogen. In certain embodiments, $R_9$ is —$OR_{12}$ and $R_{12}$ is aryl. In certain embodiments, $R_9$ is —NHC(O)$C_1$-$C_6$ alkyl. In certain embodiments, $R_9$ is —NHC(O)NHaryl. In certain embodiments, $R_9$ is —($CH_2$)$_m$$NH_2$. In certain embodiments, $R_9$ is —($CH_2$)$_m$NHC(O)$C_1$-$C_6$ alkyl.

In certain embodiments, m is 1. In certain embodiments n is 2.

In certain embodiments, disclosed herein are pharmaceutical compositions suitable for use in a human patient, comprising any of the compounds provided herein, such as a compound of formula (I) or Formula (II), and one or more pharmaceutically acceptable excipients. In certain embodiments, the pharmaceutical compositions may be used in treating or preventing a condition or disease as described herein.

Any of the disclosed compounds may be used in the manufacture of medicaments for the treatment of any diseases or conditions disclosed herein.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, “comprises,” “comprising,” “containing” and “having” and the like can have the meaning ascribed to them in U.S. Patent law and can mean “includes,” “including,” and the like; “consisting essentially of” or “consists essentially” likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term “or” is understood to be inclusive. Unless specifically stated or obvious from context, as used herein, the terms “a”, “an”, and “the” are understood to be singular or plural.

The term “and/or” is used in this disclosure to mean either “and” or “or” unless indicated otherwise.

The term “acyl” is art-recognized and refers to a group represented by the general formula hydrocarbylC(O)—, preferably alkylC(O)—.

The term “acylamino” is art-recognized and refers to an amino group substituted with an acyl group and may be represented, for example, by the formula hydrocarbylC(O)NH—.

The term “acyloxy” is art-recognized and refers to a group represented by the general formula hydrocarbylC(O)O—, preferably alkylC(O)O—.

The term “alkoxy” refers to an alkyl group, preferably a lower alkyl group, having an oxygen attached thereto. Representative alkoxy groups include methoxy, ethoxy, propoxy, tert-butoxy and the like.

The term “alkoxyalkyl” refers to an alkyl group substituted with an alkoxy group and may be represented by the general formula alkyl-O-alkyl.

The term “alkenyl”, as used herein, refers to an aliphatic group containing at least one double bond and is intended to include both “unsubstituted alkenyls” and “substituted alkenyls”, the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

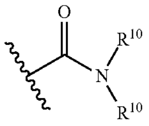

wherein each $R^{10}$ independently represents a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

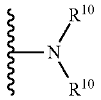

or

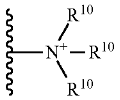

wherein each $R^{10}$ independently represents a hydrogen or a hydrocarbyl group, or two $R^{10}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

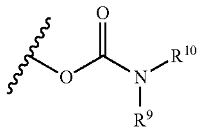

or

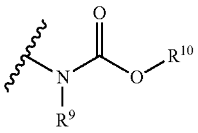

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $—OCO_2—R_{10}$, wherein $R^{10}$ represents a hydrocarbyl group.

The term "carboxy", as used herein, refers to a group represented by the formula $—CO_2H$.

The term "ester", as used herein, refers to a group $—C(O)OR_{10}$ wherein $R_{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae (i)

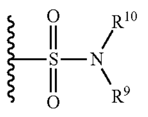

or

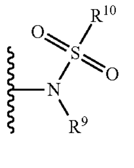

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

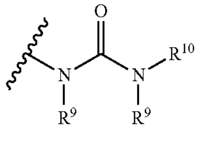

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3rd Ed., 1999, John Wiley & Sons, NY and Harrison et al., Compendium of Synthetic Organic Methods, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

The present invention includes all pharmaceutically acceptable isotopically-labelled compounds as described herein wherein one or more atoms are replaced by atoms having the same atomic number, but an atomic mass or mass number different from the atomic mass or mass number usually found in nature. In certain embodiments, compounds of the invention are enriched in such isotopically labeled substances (e.g., compounds wherein the distribution of isotopes in the compounds in the composition differ from a natural or typical distribution of isotopes).

Examples of isotopes suitable for inclusion in the compounds of the invention include isotopes of hydrogen, such as $^{2}H$ and $^{3}H$ carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds as disclosed herein, for example, those incorporating a radioactive isotope, are useful in drug and/or substrate tissue distribution studies. The radioactive isotopes tritium, i.e. $^{3}H$, and carbon-14, i.e. $^{14}C$, are useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron-emitting isotopes, such as $^{11}C$, $^{18}F$, $^{13}N$ and be useful in Positron Emission Tomography (PET) studies for examining substrate receptor occupancy.

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric race mates or mixtures of diastereoisomeric racemates. The optically active forms can be obtained for example by resolution of the racemates, by asymmetric synthesis or asymmetric chromatography (chromatography with a chiral adsorbents or eluent). That is, certain of the disclosed compounds may exist in various stereoisomeric forms.

Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. "Diastereomers" are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Diastereomeric purity by weight is the ratio of the weight of one diastereomer or over the weight of all the diastereomers. When the stereochemistry of a disclosed compound is named or depicted by structure, the named or depicted stereoisomer is at least about 60%, about 70%, about 80%, about 90%, about 99% or about 99.9% by weight relative to the other stereoisomers. When a single enantiomer is named or depicted by structure, the depicted or named enantiomer is at least about 60%, about 70%, about 80%, about 90%, about 99% or about 99.9% by weight optically pure. When a single diastereomer is named or depicted by structure, the depicted or named diastereomer is at least about 60%, about 70%, about 80%, about 90%, about 99% or about 99.9% by weight pure. Percent optical purity is the ratio of the weight of the enantiomer or over the weight of the enantiomer plus the weight of its optical isomer.

Percent purity by mole fraction is the ratio of the moles of the enantiomer (or diastereomer) or over the moles of the enantiomer (or diastereomer) plus the moles of its optical isomer. When the stereochemistry of a disclosed compound is named or depicted by structure, the named or depicted stereoisomer is at least about 60%, about 70%, about 80%, about 90%, about 99% or about 99.9% by mole fraction pure relative to the other stereoisomers. When a single enantiomer is named or depicted by structure, the depicted or named enantiomer is at least about 60%, about 70%, about 80%, about 90%, about 99% or about 99.9% by mole fraction pure. When a single diastereomer is named or depicted by structure, the depicted or named diastereomer is at least about 60%, about 70%, about 80%, about 90%, about 99% or about 99.9% by mole fraction pure.

When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

As used herein, the term "pharmaceutically acceptable salt" means any pharmaceutically acceptable salt of the compound of formula (I). For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P.H. Stahl and C.G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

In treatment, the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

Methods of Use

Ubiquitination is a post-translational modification of proteins critical to many cellular processes, including protein degradation by the proteasome, cell cycle progression, transcriptional regulation, DNA repair and signal transduction. Ubiquitination requires the sequential action of three enzymes. E1, or ubiquitin-activating enzyme, catalyzes the ATP-dependent activation of ubiquitin and formation of a thioester bond between ubiquitin C terminus and the catalytic cysteine on the E1. Ubiquitin is then transferred to a catalytic cysteine of one of the ~40 E2s (ubiquitin-conjugating enzymes) and through the E3 (ubiquitin ligase) to the substrate (Morreale and Walden, Cell, 165, 248-248e1, 2016). One E3 ubiquitin ligase is $CRL4^{DCAF15}$ where DCAF15 is a composition of DDB1- and CUL4-associated factor 15. DCAF15 is a substrate recognition (adaptor) protein of the E3 ubiquitin ligase. DDB1 recognizes UV- or chemical mutagen-induced DNA lesions. CUL4 is a cullin-RING finger ligase (CRLs) which constitute the largest family of ubiquitin ligases in eukaryotic cells. DCAF15 has been demonstrated to regulate cell proliferation, survival, DNA repair, and genomic integrity through targeted ubiquitination of key regulators (Lee and Zhou, Molecular Cell, 26, 775-780).

Numerous eukaryotic proteins containing one or more copies of a putative RNA-binding domain are known to bind single-stranded RNAs. The largest group of single strand RNA-binding proteins is the eukaryotic RNA recognition motif (RRM) family. In cancer cells, expression of numerous oncoproteins or tumor suppressors are under the control of specific RRMs. Splicing, stability, localization as well as translation of these mRNAs are highly regulated, often in a tissue-specific manner (Moore et al. *Science,* 309, 1514-1518, September 2005). Thus, RRMs are a target for degradation by an E3 ubiquitin ligase such as $CRL4^{DCAF15}$ to modulate expression of oncoproteins or tumor suppressors.

One member of the RRM family, RRM39, is composed of an arginine-serine domain at the N terminus followed by three RRMs. Aryl sulfonamides such as indisulam mediate interaction between ubiquitin ligase DCAF15 and RRM39 (Han et al. Science, 1-3, March 2017). The recruitment of RRM39 to the CUL4-DCAF15 E3 ubiquitin ligase, polyubiquitination and proteasomal degradation leads to its degradation. Mutations in RRM39 that increase its stability and prevent its recruitment to CUL4-DCAF15 have been linked to the resistance towards anti-cancer drugs such as indisulam Cancer genome sequencing efforts have identified mutations in splicing factors, and aryl sulfonamides such as indisulam provide a strategy to target this splicing. (Dvinge, et al., Nat. Rev. Cancer 16, 413-430). These mutations have been most often identified in myelodysplastic syndrome, chronic lymphocytic leukemia, and acute myeloid leukemia, highlighting the importance of RNA splicing in hematopoietic and lymphoid malignancies. These cancers are also more likely to be dependent on RRM39, suggesting that it may be a critical factor in RNA splicing (Han, et al., Science, 1-3, March 2017). Therapeutic strategies that target RNA splicing in hematopoietic and lymphoid malignancies have thus far centered on small molecule inhibitors of proteins important for splicing. One example is spliceostatin, a potent inhibitor of the splicing factor SF3B1 (Kaida, et al., Nat. Chem. Biol. 3, 576-583). Spliceostatin has shown some efficacy in clinical trials but has also been associated with adverse events (Lee, et al., Nat. Med. 22, 976-986). Drugs inducing degradation of RRM39, in contrast, appear to influence the splicing of only a subset of pre-mRNAs. Accordingly, the aryl sulfonamides disclosed herein offer the opportunity to selectively target splicing pathways important for cancer cell growth with lessened adverse reactions when compared to previous treatments.

Disclosed herein are compounds and compositions that selectively target certain RNA splicing pathways implicated in cancer cell growth by, for example, degradation of RRM family proteins including but not limited to RBM39, RBM23, U2AF1, SF3B1, SF3B4, and SRSF2.

In certain embodiments, disclosed herein are degraders of RRM proteins that are therapeutic agents in the treatment of diseases such as cancer and metastasis and other RRM protein mediated diseases.

Disclosed herein are methods of degrading RRM proteins in a cell, comprising contacting the cell with a compound of Formula (I), Formula (II), or a pharmaceutically acceptable salt thereof. In certain embodiments, the RRM protein is RRM39.

In certain embodiments, the present disclosure relates to a method of treating a disease or disorder associated with degradation of RRM proteins, comprising administering to a subject in need thereof a compound of Formula (I) or Formula (II). In certain embodiments, the RRM protein is RRM39.

In certain embodiments, the present disclosure also relates to the use of a degrader of RRM proteins in the manufacture of a medicament for treating or preventing a disease or condition mediated by RRM proteins, wherein the medicament comprises a compound of Formula (I), Formula (II), or a pharmaceutically acceptable salt thereof. In certain embodiments, the RRM protein is RRM39.

In certain embodiments, the present disclosure relates to a compound of Formula (I), Formula (II), or a pharmaceutically acceptable salt thereof, for use for treating or preventing a disease associated with degrading RRM proteins. In certain embodiments, the RRM protein is RRM39.

Disclosed herein are methods of treating a disease, comprising administering to a subject in need thereof a compound of Formula (I), Formula (II), or a pharmaceutically acceptable salt thereof.

In certain embodiments, the disease or disorder is selected from cancer and metastasis, neurodegenerative diseases, immunological disorders, diabetes, bone and joint diseases, osteoporosis, arthritis inflammatory disorders, cardiovascular diseases, myelodysplastic syndromes, ischemic diseases, viral infections and diseases, viral infectivity and/or latency, and bacterial infections and diseases.

In certain embodiments the disclosure relates to a method of treating or preventing cancer, comprising administering to a subject in need thereof of a compound of Formula (I), Formula (II), or a pharmaceutically acceptable salt thereof.

In some embodiments, exemplary cancers include, but are not limited to, including bladder cancer, bone cancer, brain cancer (including glioblastoma), breast cancer, cardiac cancer, cervical cancer, colon cancer, colorectal cancer, esophageal cancer, fibrosarcoma, gastric cancer, gastrointestinal cancer, head & neck cancer, Kaposi's sarcoma, kidney cancer (including renal cell adenocarcinoma), leukemia, liver cancer, lung cancer (including non-small cell lung cancer, small cell lung cancer, and mucoepidermoid pulmonary carcinoma), lymphoma, melanoma, myeloma, ovarian cancer (including ovarian adenocarcinoma), pancreatic cancer, penile cancer, prostate cancer, testicular germcell cancer, thymoma and thymic carcinoma, colon cancer, fibrosarcoma, kidney cancer, lung cancer, melanoma, ovarian cancer, and prostate cancer.

In some embodiments the cancer is chronic lymphocytic leukemia or acute myeloid leukemia.

Disclosed herein are methods of treating neurodegenerative diseases, comprising administering to a subject in need thereof a compound of Formula (I), Formula (II), or a pharmaceutically acceptable salt thereof.

In some embodiments, neurodegenerative diseases include, but are not limited to, Alzheimer's disease, multiple sclerosis, Huntington's disease, infectious meningitis, encephalomyelitis, Parkinson's disease, amyotrophic lateral sclerosis, or encephalitis.

Pharmaceutical Compositions

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable excipient can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable excipient, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable excipient" as used herein means a pharmaceutically acceptable material, composition or vehicle, such as a liquid or solid filler, diluent, excipient, solvent or encapsulating material. Each excipient must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, sub arachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular subject, composition, and mode of administration, without being toxic to the subject.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, about 5, about 20, about 50, about 75, about 100, about 150, about 250, about 500, about 750, about 1000, about 1250, about 2500, about 3500, or about 5000 mg of the disclosed compound, or, in a range of from one amount to another amount in the list of doses In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

The compounds of Formula (I) or Formula (II) may be prepared by methods known in the art of organic synthesis as set forth in part by the following synthetic schemes. The compounds described herein may be made from commercially available starting materials or synthesized using known organic, inorganic, and/or enzymatic processes.

In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I) or Formula (II).

Those skilled in the art will recognize if a stereocenter exists in the compounds of Formula (I) or Formula (II). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994). A mixture of enantiomers, diastereomers, cis/trans isomers resulting from the process described above can be separated into their single components by chiral salt technique, chromatography using normal phase, reverse phase or chiral column, depending on the nature of the separation.

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. All commercially available starting materials were purchased from Sigma Aldrich, Fisher Scientific, Oakwood Chemical and Combi Block. All reagents were used as received without further purification. Known compounds were synthesized according to published literature procedures and any modifications are noted. Anhydrous solvents, such as tetrahydrofuran (THF), diethyl ether, dichloromethane (DCM), dimethyl formamide (DMF), dimethylsulfoxide (DMSO), 1,4-dioxane, and toluene (PhMe) were purchased from Fisher Scientific, and used as received. If necessary, air or moisture sensitive reactions were carried out under an inert atmosphere of nitrogen.

Removal of solvents was accomplished on a Büchi R-300 rotary evaporator and further concentration was done under a Welch 1400B-01 vacuum line, and Labconco FreeZone 6 plus system. Purification of compounds was performed by normal phase column chromatography using Teledyne CombiFlash chromatography system, and/or reversed phase chromatography on Waters Micromass ZQ preparative system with SunFire® Prep C18 OBDTM 5 μM column. The purity was analyzed on Waters Acquity UPLC system. Analytical thin layer chromatography (TLC) plates were purchased from Fisher Scientific (EMD Millipore TLC Silica Gel60 F254). Visualization was accomplished by irradiation under UV light (254 nm).

All $^1$H-NMR spectra were recorded at 298K on a Bruker ARX 500 (500 MHz) spectrometer. $^{13}$C-NMR spectra were recorded on a Bruker ARX 500 (126 MHz) spectrometer. Samples were dissolved in $CDCl_3$, DMSO-d6, or $CD_3OD$. The spectra were referenced to the residual solvent peak (chloroform-d: 7.26 ppm for $^1$H-NMR and 77.16 ppm for $^{13}$C-NMR; DMSO-d6: 2.50 ppm for $^1$H-NMR and 39.25 ppm for $^{13}$C-NMR, $CD_3OD$: 3.31 ppm for $^1$H NMR and 49.00 ppm for $^{13}$C NMR or tetramethylsilane (TMS) as the internal standard. Chemical shift, multiplicity (s=singlet, d=doublet, t=triplet, q=quartet, m=multiplet, br=broad peak), coupling constants (Hz), and number of protons. Mass spectrometry (LCMS) data were obtained on Waters Acquity UPLC system in positive ESI mode.

Examples 2-16 were synthesized using the procedure described in Scheme 1 for Example 1.

Scheme 1

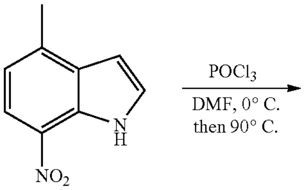

S1-1

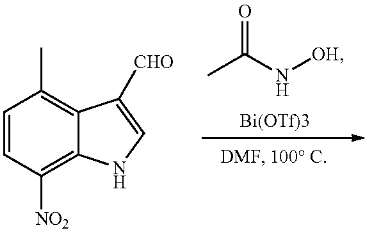

S2-2

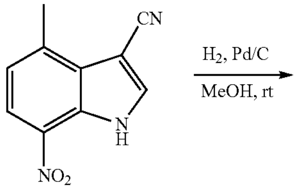

S1-3

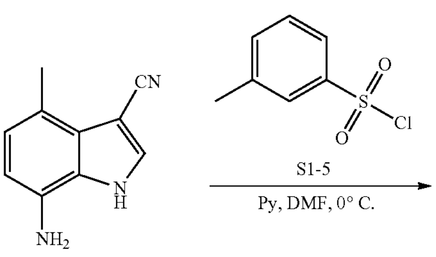

S1-4

-continued

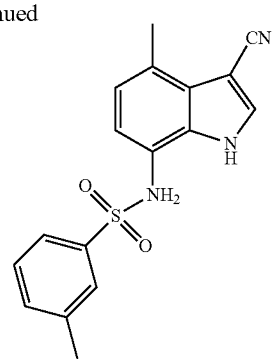

1

To a stirred solution of indole S1-1 (1.50 g, 8.52 mmol) in DMF (10 mL) at 0° C. was added $POCl_3$ (3.91 g, 25.57 mmol, 3.0 equiv) dropwise. After stirring at 90° C. for 2 h, the reaction was quenched with NaOH (2.0 M aq., 20 mL). The resulting mixture was stirred at this temperature for 1 h and then diluted with EtOAc (300 mL). The combined organic phases were washed with brine (3×200 mL), dried over anhydrous $Na_2SO_4$ and concentrated under reduced pressure to afford indolyl aldehyde S1-2 (1.63 g, 7.99 mmol, 94% yield) as a yellow solid.

A solution of S1-2 (500 mg, 2.45 mmol), N-hydroxyacetamide (239 mg, 3.18 mmol, 1.3 equiv), $Bi(OTf)_3$ (80 mg, 0.123 mmol, 0.05 equiv) in DMF (6 mL) was stirred at 100° C. for 16 h before it was diluted with EtOAc (100 mL). The resulting mixture was washed with brine (3×50 mL), dried over anhydrous $Na_2SO_4$ and concentrated under reduced pressure. The residue was used in next step without any further purification.

To a stirred solution of the above residue in MeOH (25 mL) was added Pd/C (100 mg, 20% w/w). After stirring at room temperature under 1 atm $H_2$ for 3 h, the reaction mixture was filtered. The resulting solution was concentrated under reduced pressure. The residue was purified by flash column chromatography to give S1-4 (208 mg, 1.18 mmol, 48% yield over two steps).

To a stirred solution of S1-4 (17.1 mg, 0.1 mmol) in DMF (1 mL) at 0° C. was added pyridine (15.8 mg, 0.2 mmol, 2.0 equiv) and tosyl chloride S1-5 (18.9 mg in 1 mL DMF, 0.1 mmol, 1.0 equiv). After stirring at this temperature for 0.5 h, The resulting reaction mixture was purified by Reverse-Phase HPLC to give 1 (18.0 mg, 0.055 mmol, 55% yield). $^1$H NMR (500 MHz, DMSO) δ 11.91 (s, 1H), 9.87 (s, 1H), 8.17 (d, J=3.2 Hz, 1H), 7.54 (s, 1H), 7.48 (d, J=7.2 Hz, 1H), 7.44-7.37 (m, 2H), 6.77 (dd, J=7.8, 0.7 Hz, 1H), 6.57 (d, J=7.7 Hz, 1H), 2.56 (s, 3H), 2.32 (s, 3H).

2

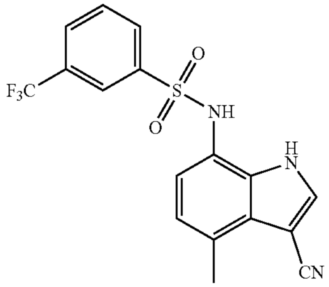

2: $^{1}$H NMR (500 MHz, DMSO) δ 12.02 (s, 1H), 10.08 (s, 1H), 8.18 (d, J=3.0 Hz, 1H), 8.03 (d, J=7.8 Hz, 1H), 7.95 (s, 1H), 7.92 (d, J=8.1 Hz, 1H), 7.77 (t, J=7.9 Hz, 1H), 6.79 (dd, J=7.7, 0.7 Hz, 1H), 6.48 (d, J=7.7 Hz, 1H), 2.57 (s, 3H).

3

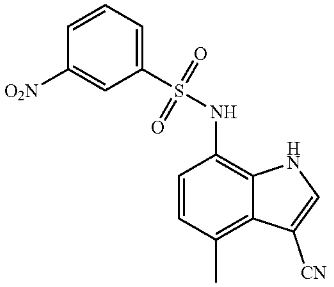

3: $^{1}$H NMR (500 MHz, DMSO) δ 12.02 (s, 1H), 10.23 (s, 1H), 8.50-8.42 (m, 2H), 8.17 (d, J=2.8 Hz, 1H), 8.04-7.93 (m, 1H), 7.80 (t, J=8.0 Hz, 1H), 6.78 (dd, J=7.8, 0.6 Hz, 1H), 6.54 (d, J=7.7 Hz, 1H), 2.57 (s, 3H).

4

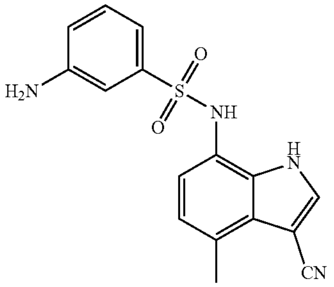

4: $^{1}$H NMR (500 MHz, DMSO) δ 11.84 (s, 1H), 9.76 (s, 1H), 8.16 (s, 1H), 7.12 (t, J=7.9 Hz, 1H), 6.88 (t, J=2.0 Hz, 1H), 6.82 (ddd, J=7.7, 1.7, 0.8 Hz, 1H), 6.78 (dd, J=7.8, 0.7 Hz, 1H), 6.70 (ddd, J=8.1, 2.2, 0.8 Hz, 1H), 6.63 (d, J=7.7 Hz, 1H), 5.52 (s, 2H), 2.56 (s, 3H).

5

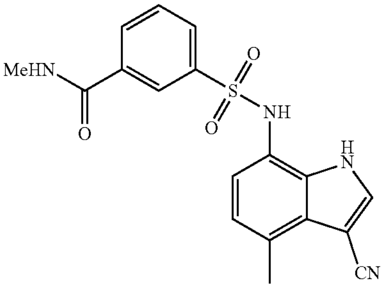

5: $^{1}$H NMR (500 MHz, DMSO) δ 11.97 (d, J=2.4 Hz, 1H), 10.01 (s, 1H), 8.65 (q, J=4.2 Hz, 1H), 8.22 (t, J=1.7 Hz, 1H), 8.17 (d, J=3.1 Hz, 1H), 8.08-7.97 (m, 1H), 7.78 (ddd, J=7.8, 1.7, 1.0 Hz, 1H), 7.61 (t, J=7.8 Hz, 1H), 6.76 (dd, J=7.8, 0.7 Hz, 1H), 6.51 (d, J=7.7 Hz, 1H), 2.78 (d, J=4.5 Hz, 3H), 2.56 (s, 3H).

6

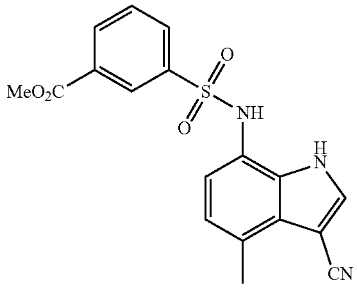

6: $^{1}$H NMR (500 MHz, DMSO) δ 11.98 (d, J=2.0 Hz, 1H), 10.07 (s, 1H), 8.27 (t, J=1.7 Hz, 1H), 8.21-8.11 (m, 2H), 7.87 (ddd, J=7.9, 1.8, 1.2 Hz, 1H), 7.68 (t, J=7.8 Hz, 1H), 6.77 (dd, J=7.7, 0.7 Hz, 1H), 6.49 (d, J=7.7 Hz, 1H), 3.88 (s, 3H), 2.56 (s, 3H).

7

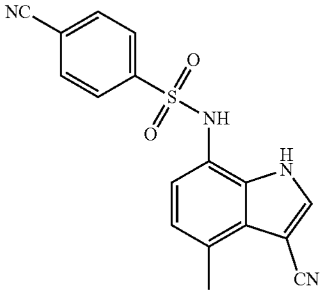

7: $^{1}$H NMR (500 MHz, DMSO) δ 12.01 (d, J=2.2 Hz, 1H), 10.20 (s, 1H), 8.19 (d, J=3.1 Hz, 1H), 8.09-7.99 (m, 2H), 7.88-7.72 (m, 2H), 6.79 (dd, J=7.7, 0.7 Hz, 1H), 6.49 (d, J=7.7 Hz, 1H), 2.58 (s, 3H).

8

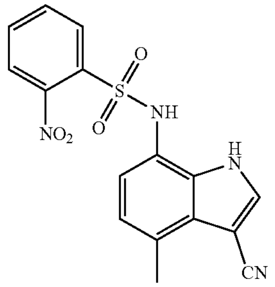

8: $^{1}$H NMR (500 MHz, DMSO) δ 12.03 (d, J=1.9 Hz, 1H), 10.32 (s, 1H), 8.21 (d, J=3.1 Hz, 1H), 7.97 (dd, J=7.9, 1.2 Hz, 1H), 7.87 (ddd, J=15.7, 7.9, 1.4 Hz, 2H), 7.78 (td, J=7.7, 1.2 Hz, 1H), 6.81 (dd, J=7.8, 0.7 Hz, 1H), 6.62 (d, J=7.7 Hz, 1H), 2.59 (s, 3H).

9

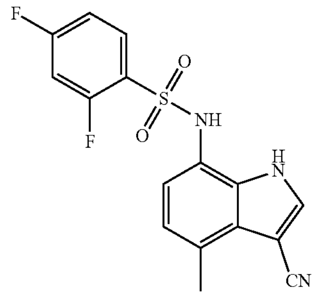

9: ¹H NMR (500 MHz, DMSO) δ 11.99 (d, J=1.9 Hz, 1H), 10.28 (s, 1H), 8.20 (d, J=3.2 Hz, 1H), 7.72 (td, J=8.6, 6.4 Hz, 1H), 7.59-7.46 (m, 1H), 7.20 (td, J=8.4, 2.2 Hz, 1H), 6.79 (dd, J=7.8, 0.6 Hz, 1H), 6.59 (d, J=7.7 Hz, 1H), 2.57 (s, 1H), 2.57 (s, 1H).

10

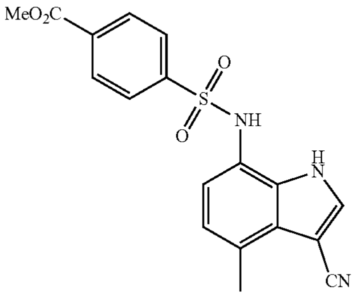

10: ¹H NMR (500 MHz, DMSO) δ 11.98 (d, J=2.3 Hz, 1H), 10.11 (s, 1H), 8.17 (d, J=3.1 Hz, 1H), 8.12-8.02 (m, 2H), 7.87-7.75 (m, 2H), 6.77 (dd, J=7.8, 0.6 Hz, 1H), 6.49 (d, J=7.7 Hz, 1H), 3.87 (s, 3H), 2.56 (s, 3H).

11

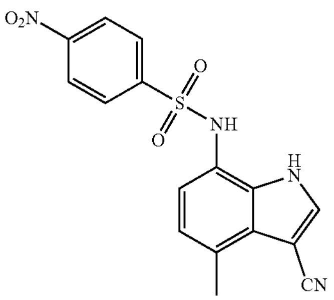

11: ¹H NMR (500 MHz, DMSO) δ 12.04 (d, J=2.1 Hz, 1H), 10.27 (s, 1H), 8.41-8.31 (m, 2H), 8.19 (d, J=3.1 Hz, 1H), 7.98-7.81 (m, 2H), 6.78 (d, J=8.0 Hz, 1H), 6.51 (d, J=7.7 Hz, 1H), 2.58 (s, 3H).

12

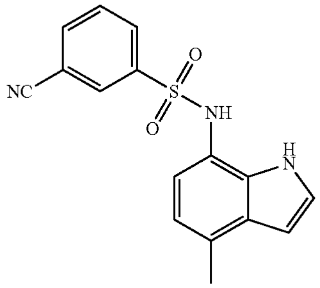

12: ¹H NMR (500 MHz, DMSO) δ 10.78 (s, 1H), 9.93 (s, 1H), 8.10 (t, J=1.5 Hz, 1H), 8.09-8.04 (m, 1H), 7.95 (ddd, J=8.0, 1.7, 1.2 Hz, 1H), 7.71 (t, J=7.9 Hz, 1H), 7.27 (t, J=2.8 Hz, 1H), 6.62 (dd, J=7.6, 0.7 Hz, 1H), 6.49 (d, J=7.6 Hz, 1H), 6.42 (dd, J=3.0, 2.0 Hz, 1H), 2.38 (s, 3H).

13

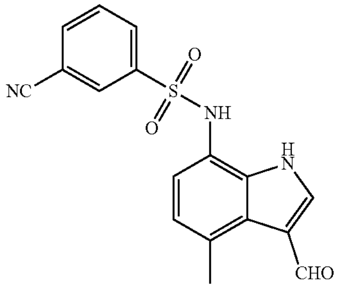

13: ¹H NMR (500 MHz, DMSO) δ 12.02 (d, J=1.1 Hz, 1H), 10.07 (s, 1H), 9.90 (s, 1H), 8.20 (d, J=3.3 Hz, 1H), 8.15-8.10 (m, 2H), 7.97-7.84 (m, 1H), 7.74 (t, J=8.1 Hz, 1H), 6.81 (d, J=8.2 Hz, 1H), 6.50 (d, J=7.7 Hz, 1H), 2.69 (s, 3H).

14

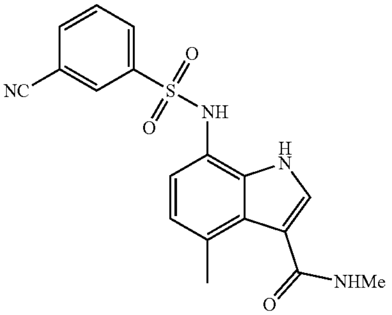

14: ¹H NMR (500 MHz, DMSO) δ 11.19 (d, J=2.3 Hz, 1H), 9.97 (s, 1H), 8.12 (t, J=1.5 Hz, 1H), 8.12-8.07 (m, 1H), 7.98-7.89 (m, 2H), 7.73 (t, J=7.9 Hz, 1H), 7.59 (d, J=2.9 Hz, 1H), 6.68-6.62 (m, 1H), 6.43 (d, J=7.7 Hz, 1H), 2.72 (d, J=4.6 Hz, 3H), 2.50 (s, 3H).

Scheme 2

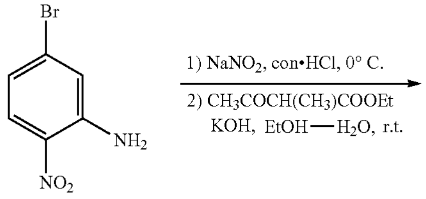

S2-1

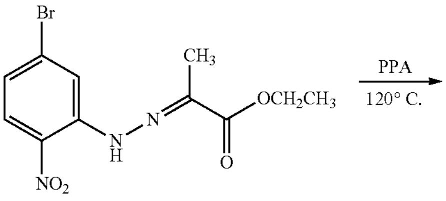

S2-2

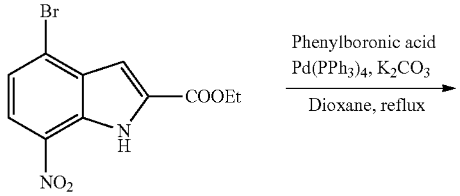

S2-3

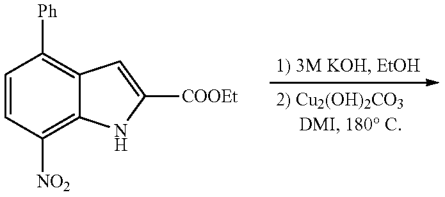

S2-4

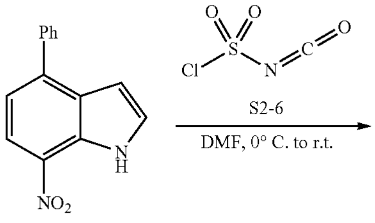

S2-5

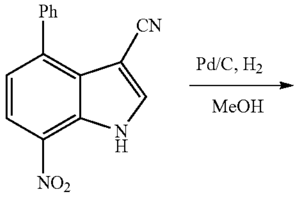

S2-7

-continued

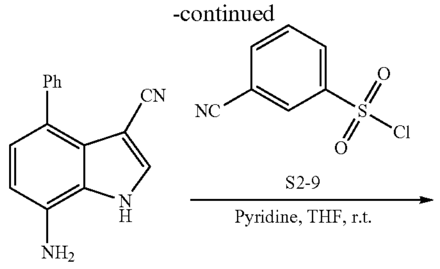

S2-8

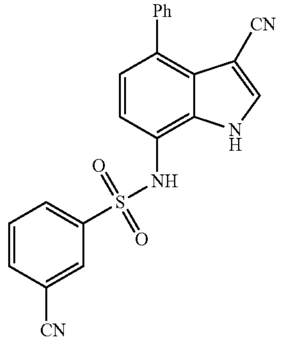

15

To a mixture of 5-bromo-2-nitroaniline (5 g, 23 mmol) in 9 mL water and 8 mL concentrated aqueous hydrochloric acid in the ice bath was added a solution of sodium nitrite (1.7 g, 30 mmol) in 5 mL water dropwise. Then, another flask, 50% potassium hydroxide (3.1 g, 69 mmol) was slowly added to a solution of ethyl-2-methyl-3-oxobutanoate (3.3 g, 23 mmol) in 20 mL EtOH. To this mixture was added 40 mL ice water, stirred for 30 min. The diazonium solution was dropped to the later solution, continue stirring 30 min. The precipitate was filtered and wash with water, the solid was dried by vacuum drier to give title compound S2-2 (3.9 g, 53%).

A mixture of hydrazine S2-2 (1.9 g, 5.7 mmol) and 7.5 g polyphosphoric acid was heated at 120° C. for 1 h. The reaction mixture was poured into water and stirred 30 min, then extracted with dichloromethane. The solvent was evaporated, the crude product was recrystallized by ethanol to get indole S2-3 (1.1 g, 61%).

To a deoxygenated mixture of indole S2-3 (940 mg, 3 mmol), phenylboronic acid (550 mg, 4.5 mmol) and potassium carbonate (1.0 g, 7.5 mmol) in 30 mL dioxane and 6 mL water, $Pd(PPh_3)_4$ (470 mg, 0.6 mmol) was added. The resulting mixture was heated at 100° C. for 5 h. The mixture was diluted with 60 mL EtOAc and 30 mL water. The aqueous phase was extracted with EtOAc (30 mL×3). Combined the organic layer was dried over $MgSO_4$. The residue was purified by flash column chromatography to give S2-4.

To a mixture of indole S2-4 (350 mg, 1.1 mmol) in 4 mL ethanol was added a 3 M potassium hydroxide (2 mL), the resulting mixture was stirred at 50° C. for 3 h. Then evaporation of ethanol, the mixture was acidified to PH<5 with 3M hydrochloric acid. The aqueous phase was extracted with EtOAc (20 mL×3). Combined the organic layer was dried over $MgSO_4$, concentrated to give carboxylic acid without further purified. The carboxylic acid intermediate was dissolved in 5 mL DMI, then $Cu_2(OH)CO_3$ (370 mg, 1.6 mmol) was added, the resulting mixture was heated to 180° C. for 1 h. The reaction was cooled to r.t., water and EtOAc was added, separated the organic phase, washed with brine (15 mL×2), dried over anhydrous $MgSO_4$ and concentrated under reduced pressure. The residue was purified by flash column chromatography to give S2-5.

To a solution of S2-5 (100 mg, 0.42 mmol) in 2 mL DMF at 0° C. was added chlorosulfonyl-isocyanate (75 mg, 0.53 mmol). The mixture was then stirred at room temperature overnight, poured into 20 mL ice water and stirred for another 2 h, then 20 mL EtOAc was added, separated the organic phase, washed with brine (15 mL×2), dried over anhydrous $MgSO_4$ and concentrated under reduced pressure. The residue was purified by flash column chromatography to give compound S2-7.

To a solution of S2-7 (50 mg, 0.19 mmol) in 5 mL MeOH was added Pd/C (10 mg, 20% w/w). After stirring at room temperature under 1 atm H2 for 3 h, the reaction mixture was filtered. The resulting solution was concentrated under reduced pressure to give S2-8 without further purification.

To a stirred solution of S2-8 (40 mg, 0.17 mmol) in 2 mL THF at r.t. was added pyridine (27 mg, 0.34 mmol) and 3-cyano-sulfonyl chloride 15 (45 mg, 0.22 mmol in 2 mL THF). After stirring at this temperature for 1 h, The resulting reaction mixture was purified by Reverse-Phase HPLC to give 15.

$^1H$ NMR (500 MHz, DMSO) δ 12.20 (d, J=2.3 Hz, 1H), 10.34 (s, 1H), 8.27 (d, J=3.2 Hz, 1H), 8.19 (t, J=1.6 Hz, 1H), 8.13 (dt, J=7.7, 1.2 Hz, 1H), 8.03 (dt, J=7.7, 1.2 Hz, 1H), 7.77 (t, J=7.9 Hz, 1H), 7.48-7.37 (m, 5H), 6.98 (d, J=7.8 Hz, 1H), 6.80 (d, J=7.8 Hz, 1H).

16

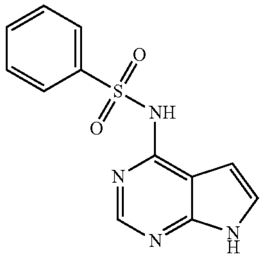

16: $^1H$ NMR (500 MHz, DMSO) δ 8.15 (s, 1H), 8.09 (d, J=1.0 Hz, 1H), 8.08 (t, J=1.6 Hz, 1H), 7.67-7.62 (m, 2H), 7.57 (d, J=4.0 Hz, 1H), 7.40 (s, 2H), 6.85 (d, J=4.0 Hz, 1H), 6.85 (d, J=4.0 Hz, 1H).

17

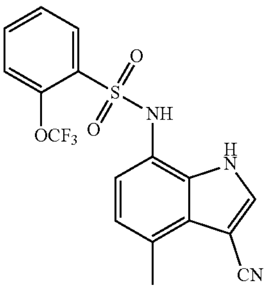

17: $^1H$ NMR (500 MHz, DMSO) δ 11.97 (s, 1H), 10.15 (s, 1H), 8.20 (d, J=3.1 Hz, 1H), 7.87-7.67 (m, 2H), 7.56 (d, J=8.4 Hz, 1H), 7.52-7.43 (m, 1H), 6.83-6.67 (d, J=7.7 Hz, 1H), 6.51 (d, J=7.7 Hz, 1H), 2.56 (s, 3H).

18

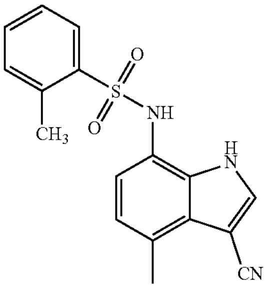

18: $^1H$ NMR (500 MHz, DMSO) δ 11.94 (s, 1H), 9.94 (s, 1H), 8.19 (s, 1H), 7.72-7.28 (m, 4H), 6.73-6.72 (d, J=7.9 Hz, 1H), 6.49 (d, J=7.9 Hz, 1H), 2.55 (s, 3H), 2.54 (s, 3H).

19

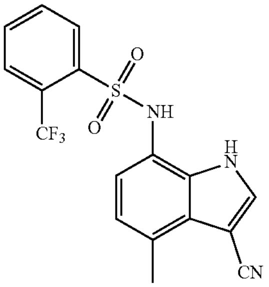

19: $^1H$ NMR (500 MHz, DMSO) δ 12.01 (s, 1H), 10.20 (s, 1H), 8.21 (s, 1H), 8.04-7.93 (m, 2H), 7.88-7.76 (m, 2H), 6.75 (dt, J=15.8, 7.9 Hz, 1H), 6.51 (dd, J=12.6, 7.9 Hz, 1H), 2.57 (s, 3H).

20

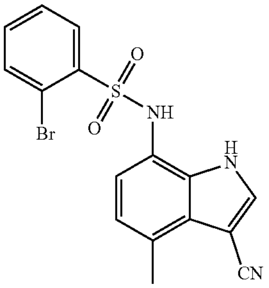

20: $^1H$ NMR (500 MHz, DMSO) δ 11.99 (s, 1H), 10.23 (s, 1H), 8.21 (s, 1H), 7.94-7.90 (m, 1H), 7.88-7.83 (m, 1H), 7.57-7.47 (m, 2H), 6.74 (dd, J=7.8, 0.7 Hz, 1H), 6.57 (d, J=7.8 Hz, 1H), 2.54 (s, 3H).

21

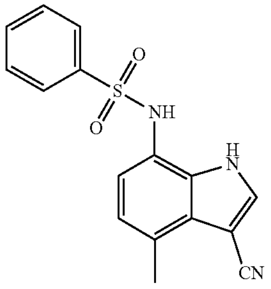

21: $^1$H NMR (500 MHz, DMSO) δ 11.91 (s, 1H), 9.92 (s, 1H), 8.16 (s, 1H), 7.69 (dd, J=5.2, 3.3 Hz, 2H), 7.66-7.56 (m, 1H), 7.52 (dd, J=10.6, 4.8 Hz, 2H), 6.77 (dd, J=7.8, 0.7 Hz, 1H), 6.55 (d, J=7.7 Hz, 1H), 2.56 (s, 3H).

22

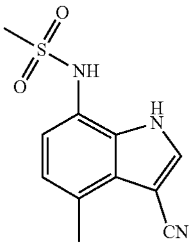

22: $^1$H NMR (500 MHz, DMSO) δ 11.93 (s, 1H), 9.36 (s, 1H), 8.21 (s, 1H), 7.09 (d, J=7.7 Hz, 1H), 6.97 (dd, J=7.7, 0.7 Hz, 1H), 2.97 (s, 3H), 2.63 (s, 3H).

23

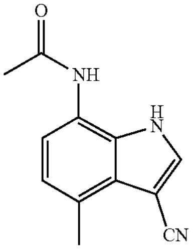

23: $^1$H NMR (500 MHz, DMSO) δ 12.46 (s, 1H), 9.79 (s, 1H), 8.30 (s, 1H), 7.09 (d, J=7.6 Hz, 1H), 7.03 (dd, J=7.6, 0.8 Hz, 1H), 2.69 (s, 3H), 2.17 (s, 3H).

24

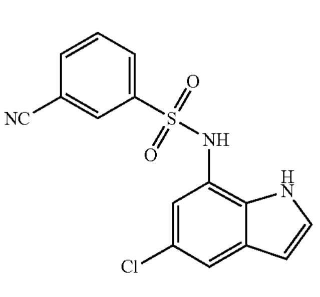

24: $^1$H NMR (500 MHz, DMSO) δ 10.97 (s, 1H), 10.31 (s, 1H), 8.16 (t, J=1.6 Hz, 1H), 8.13-8.09 (m, 1H), 7.99 (ddd, J=8.0, 1.7, 1.2 Hz, 1H), 7.75 (t, J=7.9 Hz, 1H), 7.43 (d, J=1.8 Hz, 1H), 7.39 (t, J=2.8 Hz, 1H), 6.67 (d, J=1.9 Hz, 1H), 6.42 (dd, J=3.0, 2.0 Hz, 1H).

25

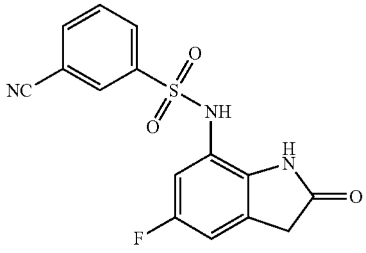

25: $^1$H NMR (500 MHz, DMSO) ε 9.95 (s, 1H), 9.87 (s, 1H), 8.20 (t, J=1.5 Hz, 1H), 8.17-8.09 (m, 1H), 8.04-7.97 (m, 1H), 7.78 (t, J=7.9 Hz, 1H), 6.99 (dd, J=7.9, 2.0 Hz, 1H), 6.68 (dd, J=10.7, 2.5 Hz, 1H), 3.50 (s, 2H).

26

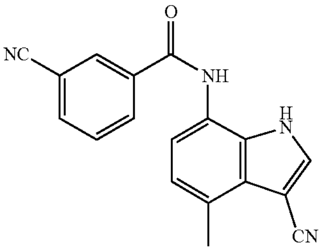

26: $^1$H NMR (500 MHz, DMSO) δ 12.00 (s, 1H), 10.44 (s, 1H), 8.49 (s, 1H), 8.32 (d, J=8.0 Hz, 1H), 8.27 (s, 1H), 8.09 (dd, J=5.1, 3.8 Hz, 1H), 7.79 (t, J=7.8 Hz, 1H), 7.27 (d, J=7.6 Hz, 1H), 7.03-6.95 (m, 1H), 2.67 (s, 3H).

27

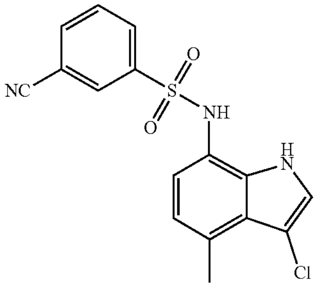

27: $^1$H NMR (500 MHz, DMSO) δ 11.08 (d, J=1.9 Hz, 1H), 9.97 (s, 1H), 8.14-8.05 (m, 2H), 7.97-7.89 (m, 1H), 7.72 (t, J=7.8 Hz, 1H), 7.39 (d, J=2.8 Hz, 1H), 6.64 (dd, J=7.7, 0.8 Hz, 1H), 6.50 (d, J=7.6 Hz, 1H), 2.60 (s, 3H).

28

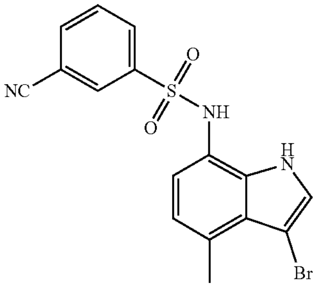

28: $^{1}H$ NMR (500 MHz, DMSO) δ 11.21 (s, 1H), 9.98 (s, 1H), 8.17-8.03 (m, 2H), 8.03-7.85 (m, 1H), 7.78-7.60 (m, 1H), 7.43 (d, J=2.8 Hz, 1H), 6.65 (dd, J=7.7, 0.8 Hz, 1H), 6.55-6.46 (m, 1H), 2.64 (s, 3H).

29

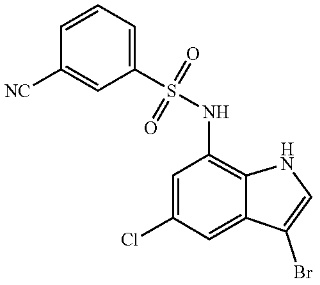

29: $^{1}H$ NMR (500 MHz, DMSO) δ 11.41 (s, 1H), 10.40 (s, 1H), 8.18 (t, J=1.6 Hz, 1H), 8.12 (dd, J=7.7, 1.1 Hz, 1H), 7.98 (ddd, J=8.0, 1.7, 1.2 Hz, 1H), 7.75 (t, J=7.9 Hz, 1H), 7.62 (d, J=2.7 Hz, 1H), 7.25 (d, J=1.4 Hz, 1H), 6.74 (d, J=1.9 Hz, 1H).

30

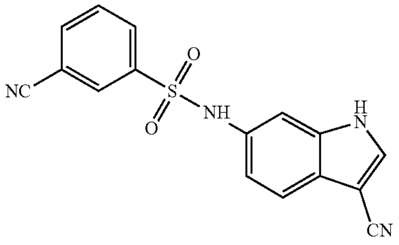

30: $^{1}H$ NMR (500 MHz, DMSO) δ 12.01 (s, 1H), 10.37 (s, 1H), 8.12 (d, J=2.9 Hz, 1H), 8.07 (t, J=1.5 Hz, 1H), 8.05-7.97 (m, 1H), 7.89 (ddd, J=8.0, 1.7, 1.2 Hz, 1H), 7.67 (t, J=7.9 Hz, 1H), 7.44 (d, J=8.5 Hz, 1H), 7.24 (d, J=1.7 Hz, 1H), 6.90 (dd, J=8.6, 1.9 Hz, 1H).

31

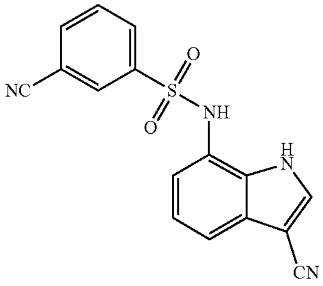

31: $^{1}H$ NMR (500 MHz, DMSO) δ 12.02 (s, 1H), 10.29 (s, 1H), 8.22 (d, J=3.1 Hz, 1H), 8.15-8.08 (m, 2H), 7.94 (ddd, J=8.0, 1.7, 1.2 Hz, 1H), 7.74 (t, J=7.9 Hz, 1H), 7.49 (d, J=7.9 Hz, 1H), 7.09 (dd, J=10.2, 5.4 Hz, 1H), 6.72 (dd, J=7.6, 0.7 Hz, 1H).

32

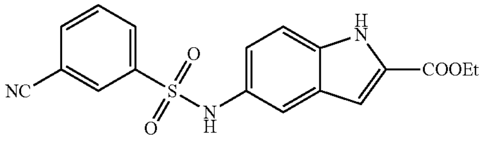

32: $^{1}H$ NMR (500 MHz, DMSO) δ 11.90 (s, 1H), 10.15 (s, 1H), 8.14-8.00 (m, 2H), 7.92 (ddd, J=7.3, 4.2, 2.9 Hz, 1H), 7.76-7.68 (m, 1H), 7.41-7.28 (m, 2H), 7.09 (d, J=1.6 Hz, 1H), 6.98 (dd, J=8.9, 1.9 Hz, 1H), 4.32 (q, J=7.1 Hz, 2H), 1.32 (t, J=7.1 Hz, 3H).

33

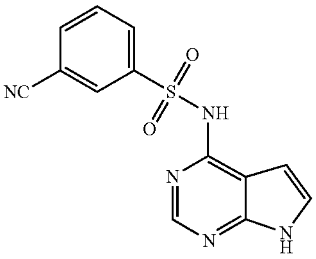

33: $^{1}H$ NMR (500 MHz, DMSO) δ 8.59 (t, J=1.6 Hz, 1H), 8.42 (ddd, J=8.1, 1.9, 1.1 Hz, 1H), 8.28 (s, 1H), 8.27-8.22 (m, 1H), 7.98 (s, 1H), 7.88 (t, J=8.0 Hz, 1H), 7.68 (d, J=4.0 Hz, 1H), 6.96 (d, J=4.0 Hz, 1H).

34

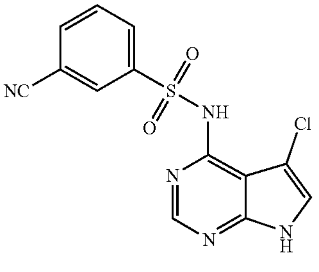

34: $^{1}$H NMR (500 MHz, DMSO) δ 8.36 (s, 1H), 8.31 (d, J=8.1 Hz, 1H), 8.08 (d, J=7.8 Hz, 1H), 8.03 (s, 1H), 7.76 (t, J=7.9 Hz, 1H), 7.20 (s, 1H), 6.90 (m, 1H).

35

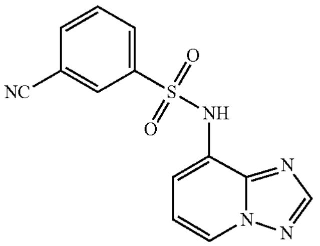

35: $^{1}$H NMR (500 MHz, DMSO) δ 8.74 (dd, J=6.7, 0.8 Hz, 1H), 8.45 (s, 1H), 8.36 (t, J=1.5 Hz, 1H), 8.16 (ddd, J=8.0, 1.7, 1.2 Hz, 1H), 8.13-8.07 (m, 1H), 7.75 (t, J=7.9 Hz, 1H), 7.50 (dd, J=7.7, 0.7 Hz, 1H), 7.13 (dd, J=14.7, 7.4 Hz, 1H).

36

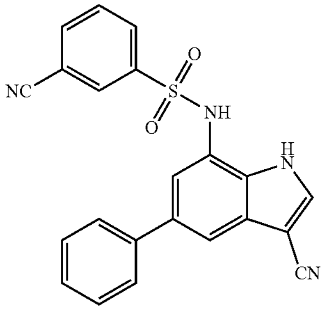

36: $^{1}$H NMR (500 MHz, DMSO) δ 12.11 (d, J=2.1 Hz, 1H), 10.39 (s, 1H), 8.27 (d, J=3.1 Hz, 1H), 8.19 (d, J=1.5 Hz, 1H), 8.15 (d, J=7.8 Hz, 1H), 8.00 (dd, J=5.4, 4.0 Hz, 1H), 7.78 (t, J=7.9 Hz, 1H), 7.70 (d, J=1.2 Hz, 1H), 7.47-7.41 (m, 4H), 7.39-7.31 (m, 1H), 6.92 (d, J=1.4 Hz, 1H).

37

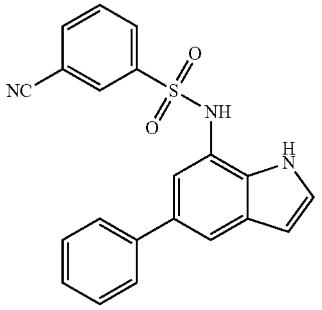

37: $^{1}$H NMR (500 MHz, DMSO) δ 10.90 (s, 1H), 10.18 (s, 1H), 8.18 (t, J=1.6 Hz, 1H), 8.13-8.09 (m, 1H), 8.06-8.01 (m, 1H), 7.76 (t, J=7.9 Hz, 1H), 7.66 (t, J=4.6 Hz, 1H), 7.40 (dd, J=12.4, 3.6 Hz, 4H), 7.36 (dd, J=5.7, 2.9 Hz, 1H), 7.33-7.26 (m, 1H), 6.89 (d, J=1.5 Hz, 1H), 6.49 (dd, J=3.0, 1.9 Hz, 1H).

38

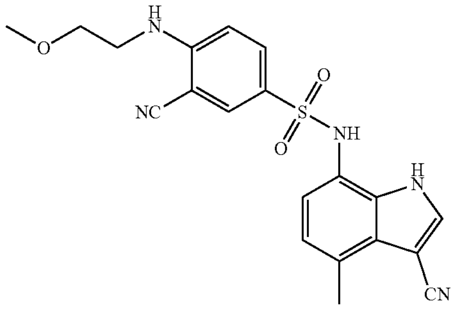

38: $^{1}$H NMR (500 MHz, DMSO) δ 11.91 (d, J=2.5 Hz, 1H), 9.70 (s, 1H), 8.18 (d, J=3.1 Hz, 1H), 7.71 (d, J=2.2 Hz, 1H), 7.56 (dd, J=9.1, 2.2 Hz, 1H), 7.08-6.73 (m, 3H), 6.64 (d, J=7.7 Hz, 1H), 3.48 (t, J=5.6 Hz, 2H), 3.40 (q, J=5.6 Hz, 2H), 3.26 (s, 3H), 2.58 (s, 3H).

39

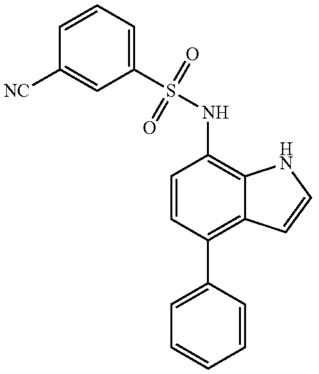

39: $^{1}$H NMR (500 MHz, DMSO) δ 11.00 (s, 1H), 10.18 (s, 1H), 8.19 (t, J=1.6 Hz, 1H), 8.13-8.09 (m, 1H), 8.08-8.01 (m, 1H), 7.81-7.72 (m, 1H), 7.60 (dd, J=8.2, 1.1 Hz, 2H), 7.47 (t, J=7.7 Hz, 2H), 7.41-7.32 (m, 2H), 6.96 (d, J=7.8 Hz, 1H), 6.75 (dd, J=7.8, 4.1 Hz, 1H), 6.54 (dd, J=3.1, 2.0 Hz, 1H).

40

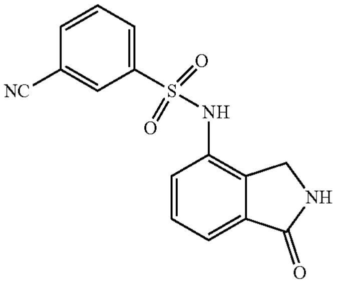

40: $^{1}$H NMR (500 MHz, DMSO) δ 10.43 (s, 1H), 8.55 (s, 1H), 8.22-8.10 (m, 2H), 8.07-7.92 (m, 1H), 7.79 (t, J=7.9 Hz, 1H), 7.49 (d, J=6.9 Hz, 1H), 7.42 (t, J=7.7 Hz, 1H), 7.25 (dd, J=7.8, 0.6 Hz, 1H), 4.16 (s, 2H).

41

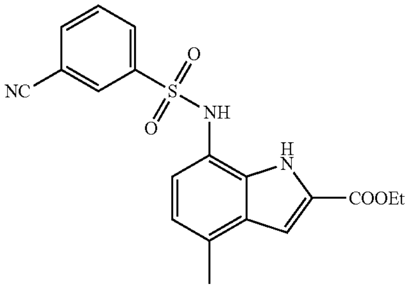

41: $^1$H NMR (500 MHz, DMSO) δ 11.30 (s, 1H), 10.01 (s, 1H), 8.18 (t, J=1.5 Hz, 1H), 8.03 (d, J=7.8 Hz, 1H), 7.97-7.93 (m, 1H), 7.66 (t, J=7.9 Hz, 1H), 7.14 (d, J=2.1 Hz, 1H), 7.10 (d, J=7.7 Hz, 1H), 6.81 (d, J=7.7 Hz, 1H), 4.35 (q, J=7.1 Hz, 2H), 2.41 (s, 3H), 1.35 (t, J=7.1 Hz, 3H).

42

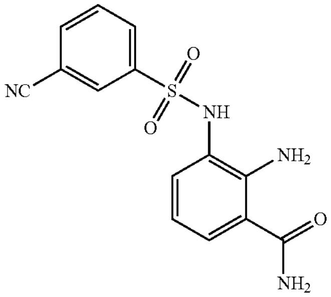

42: $^1$H NMR (500 MHz, DMSO) δ 9.60 (s, 1H), 8.13 (tt, J=4.6, 1.3 Hz, 1H), 8.09 (t, J=1.5 Hz, 1H), 7.98 (ddd, J=8.0, 1.7, 1.2 Hz, 1H), 7.84-7.75 (m, 2H), 7.47 (dd, J=8.0, 1.4 Hz, 1H), 7.20 (s, 1H), 6.75 (dd, J=7.7, 1.4 Hz, 1H), 6.41 (t, J=7.8 Hz, 1H).

43

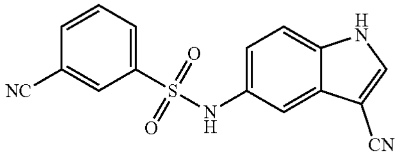

43: $^1$H NMR (500 MHz, DMSO) δ 12.21 (s, 1H), 10.32 (s, 1H), 8.22 (d, J=3.0 Hz, 1H), 8.14-8.04 (m, 2H), 7.98-7.93 (m, 1H), 7.74 (t, J=7.9 Hz, 1H), 7.44 (d, J=8.7 Hz, 1H), 7.28 (d, J=1.8 Hz, 1H), 7.02 (dd, J=8.7, 2.0 Hz, 1H).

44

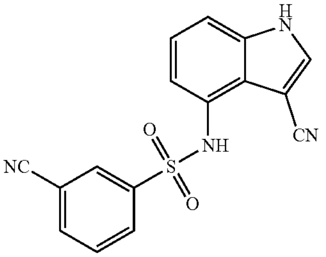

44: $^1$H NMR (500 MHz, DMSO) δ 12.28 (s, 1H), 10.21 (s, 1H), 8.23 (d, J=3.0 Hz, 1H), 8.13 (d, J=7.8 Hz, 1H), 8.06 (s, 1H), 7.91 (d, J=8.1 Hz, 1H), 7.75 (t, J=7.9 Hz, 1H), 7.45 (d, J=8.2 Hz, 1H), 7.12 (t, J=7.9 Hz, 1H), 6.53 (d, J=7.5 Hz, 1H).

45

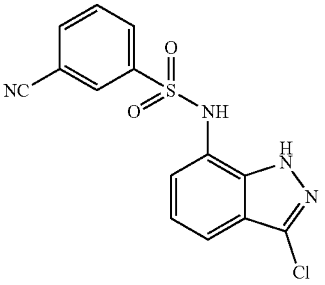

45: $^1$H NMR (500 MHz, DMSO) δ 13.19 (s, 1H), 10.39 (s, 1H), 8.18 (s, 1H), 8.13 (d, J=8.0 Hz, 1H), 7.98 (d, J=8.0 Hz, 1H), 7.75 (t, J=8.0 Hz, 1H), 7.51 (d, J=8.0 Hz, 1H), 7.08 (t, J=7.5 Hz, 1H), 6.89 (d, J=7.5 Hz, 1H)

Biochemical Assay

Increasing concentrations of compounds were added to pre-mixed biotinylated DCAF15 at 200 nM, Bodipy-FL-labelled RRM2 domain in RBM39 at 200 nM, and terbium (Tb)-coupled streptavidin at 2 nM (Invitrogen) in 384-well microplates in a buffer containing 50 mM Tris pH 7.5, 100 mM NaCl, 0.1% pluronic acid and 2% DMSO. Before TR-FRET measurements were conducted, the reactions were incubated for 15 min at room temperature. After excitation of terbium (Tb) fluorescence at 337 nm, emission at 490 nm (Tb) and 520 nm (Bodipy-FL) were recorded with a 70 μs delay to reduce background fluorescence and the reaction was followed over 1 h by recording 60 technical replicates of each data point using a PHERAstar FS microplate reader (BMG Labtech). The TR-FRET signal of each data point was extracted by calculating the 520/490 nm ratio. Data were analyzed with GraphPad Prism 7.

Table 1: DCAF15 activity of compounds of the disclosure in assay. +++ indicates an $EC_{50}$ of less than about 1 μm, ++ indicates an $EC_{50}$ between about 1 μM and about 10 μM, and + indicates an $EC_{50}$ greater than 10 μM.

TABLE 1

| Compound | $EC_{50}$ (μM) |
|---|---|
| 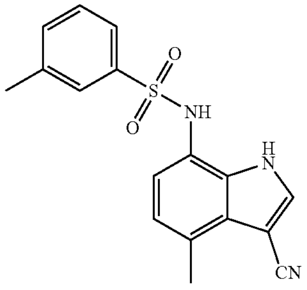 1 | ++ |

TABLE 1-continued
| Compound | $EC_{50}$ (μM) |
|---|---|
| 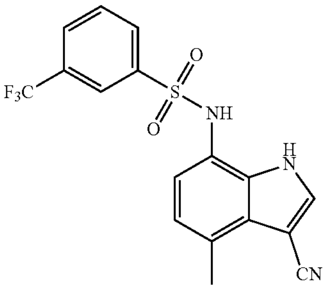 2 | ++ |
| 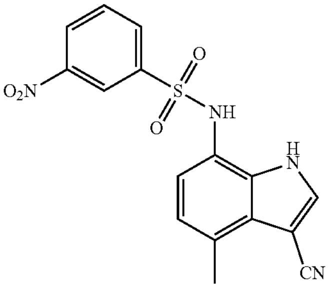 3 | ++ |
| 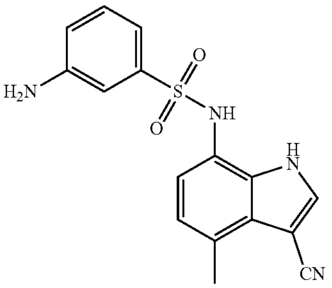 4 | ++ |
| 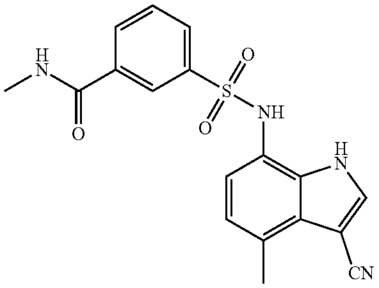 5 | ++ |
| 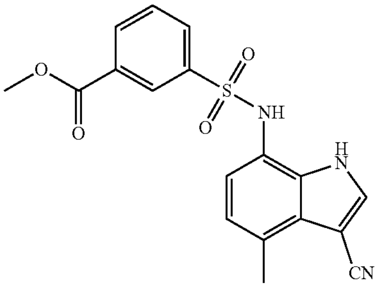 6 | ++ |
| 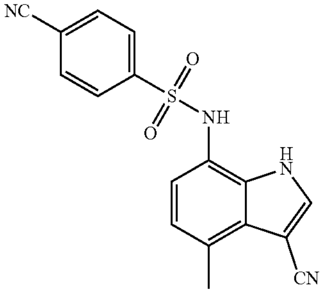 7 | ++ |
| 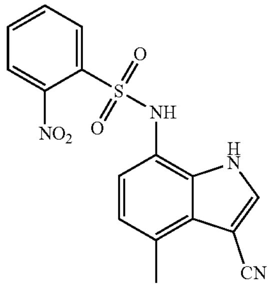 8 | + |
| 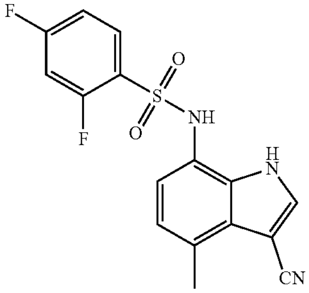 9 | ++ |

TABLE 1-continued
| Compound | $EC_{50}$ (μM) |
|---|---|
| 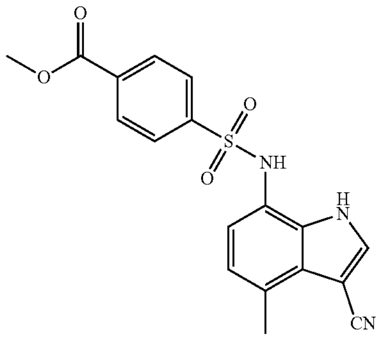 10 | ++ |
| 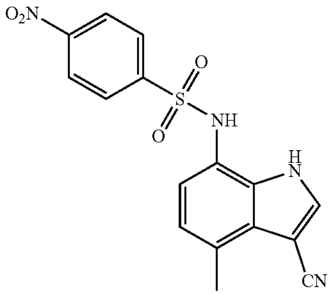 11 | ++ |
| 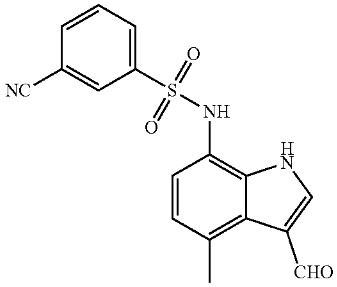 12 | ++ |
| 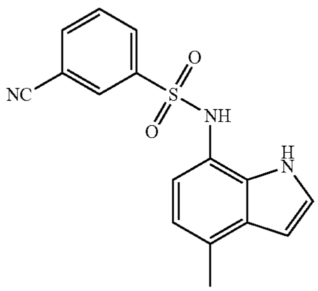 13 | + |
TABLE 1-continued
| Compound | $EC_{50}$ (μM) |
|---|---|
| 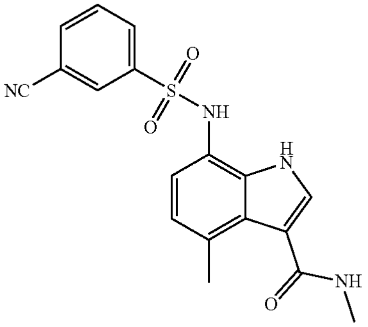 14 | + |
| 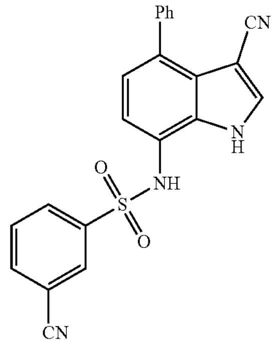 15 | + |
| 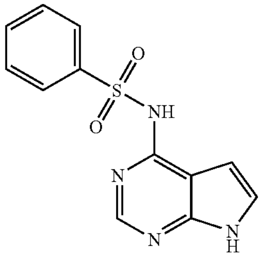 16 | + |
| 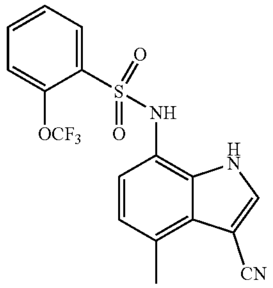 17 | + |

TABLE 1-continued
| Compound | $EC_{50}$ (μM) |
|---|---|
| 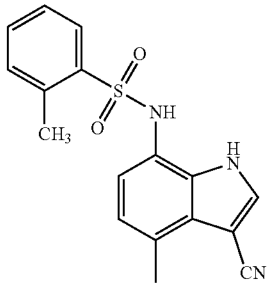 18 | + |
| 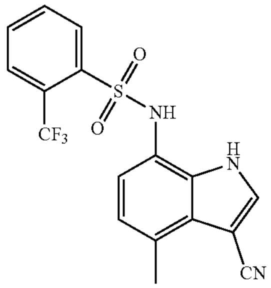 19 | + |
| 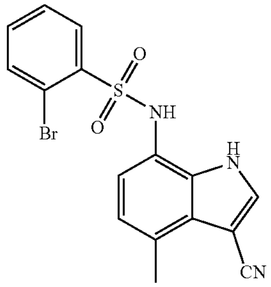 20 | + |
| 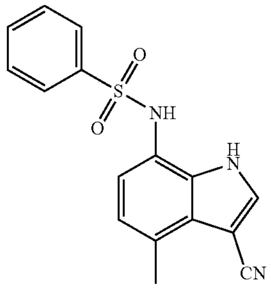 21 | ++ |
TABLE 1-continued
| Compound | $EC_{50}$ (μM) |
|---|---|
| 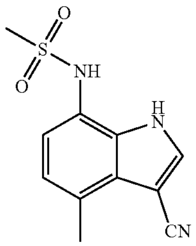 22 | + |
| 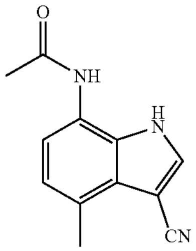 23 | + |
| 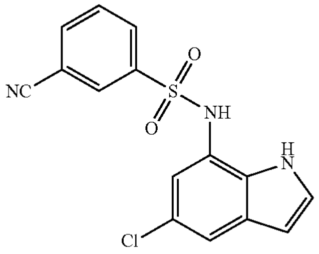 24 | + |
| 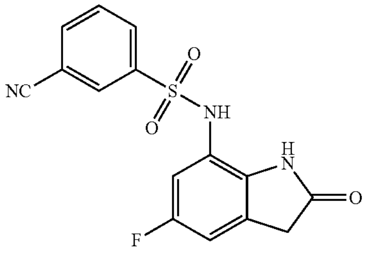 25 | + |
| 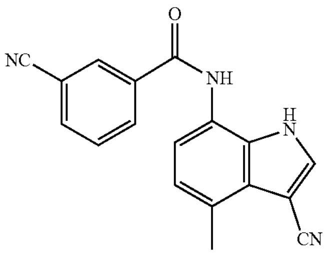 26 | + |

TABLE 1-continued
| Compound | $EC_{50}$ (μM) |
| --- | --- |
| 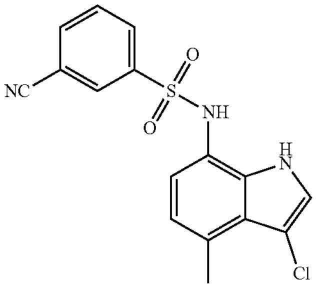 27 | ++ |
| 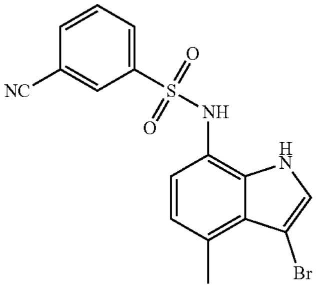 28 | ++ |
| 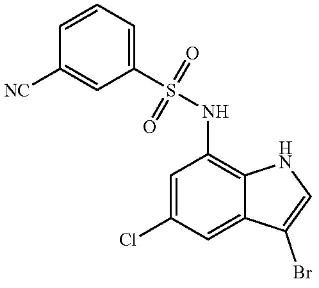 [SMILES: N#Cc1cccc(S(=O)(=O)Nc2cc(Cl)cc3cc[nH]c23)c1] 29 | + |
| 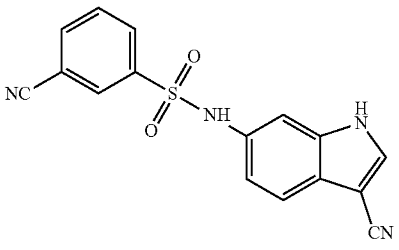 30 | + |
TABLE 1-continued
| Compound | $EC_{50}$ (μM) |
| --- | --- |
| 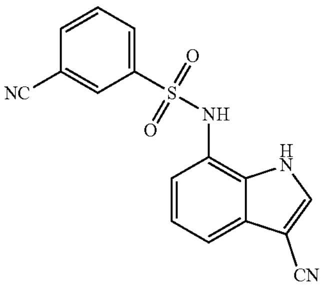 31 | + |
| 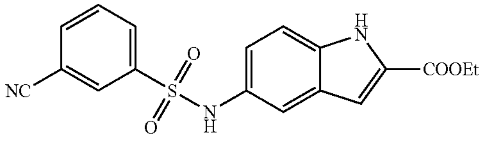 32 | + |
| 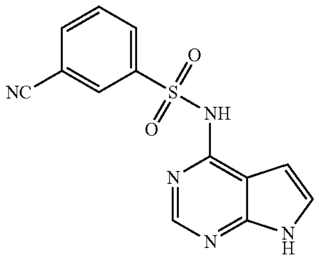 33 | + |
| 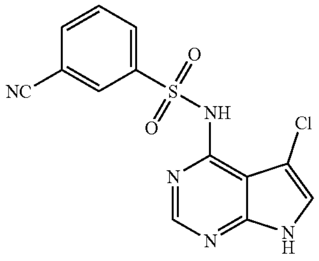 34 | + |
| 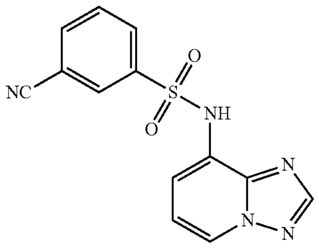 35 | + |

TABLE 1-continued
| Compound | $EC_{50}$ (μM) |
| --- | --- |
| 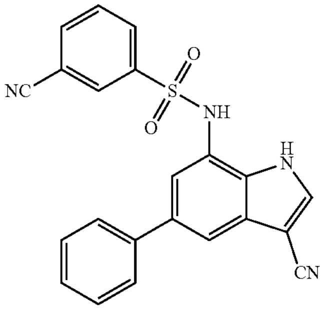 36 | + |
| 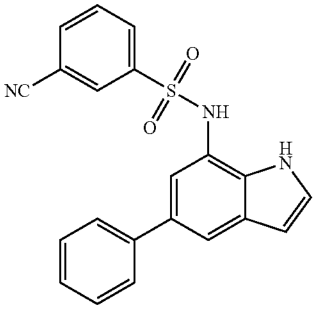 37 | + |
| 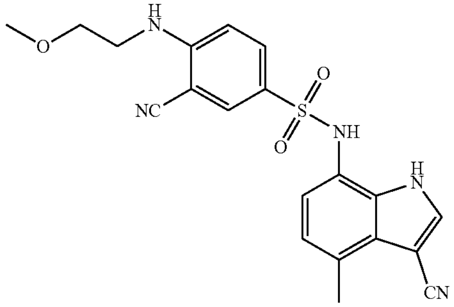 38 | ++ |
| 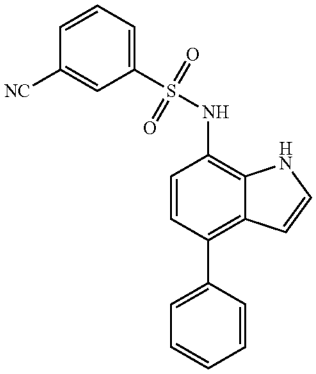 39 | + |
| 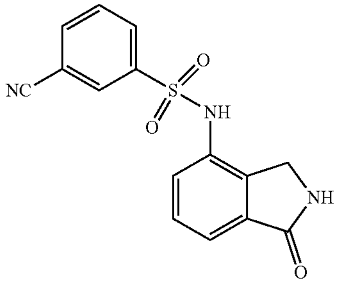 40 | + |
| 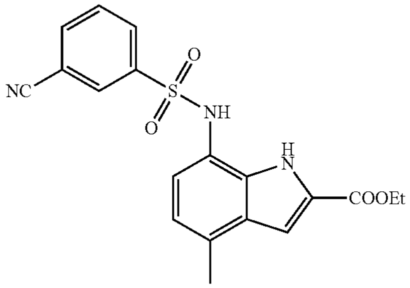 41 | + |
| 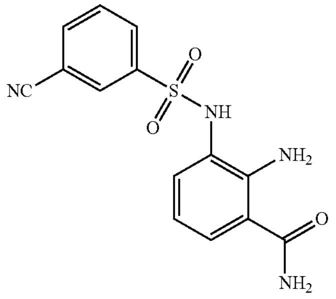 42 | + |
| 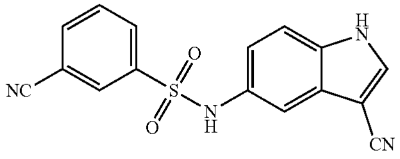 43 | + |
| 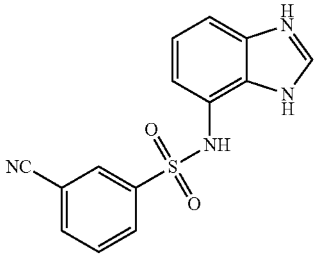 44 | + |

TABLE 1-continued
| Compound | $EC_{50}$ (μM) |
| --- | --- |
| 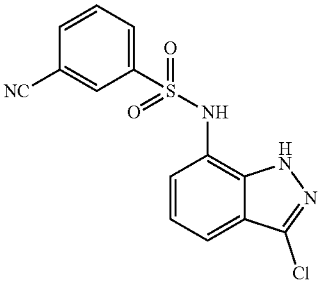 45 | + |
Further exemplary compounds include, but are not limited to, those given in Table 2.
TABLE 2
| Compound | |
| --- | --- |
| 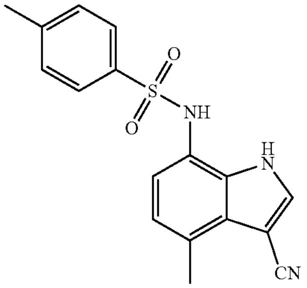 [SMILES: Cc1ccc(S(=O)(=O)Nc2ccc(C)c3c(C#N)c[nH]c23)cc1] | P1 |
| 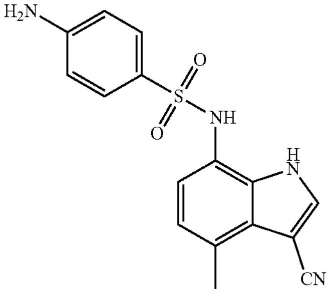 [SMILES: Cc1ccc(NS(=O)(=O)c2ccc(N)cc2)c2[nH]cc(C#N)c12] | P2 |
| 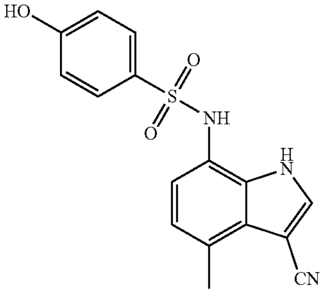 [SMILES: Cc1ccc(NS(=O)(=O)c2ccc(O)cc2)c2[nH]cc(C#N)c12] | P3 |
TABLE 2-continued
| Compound | |
| --- | --- |
| 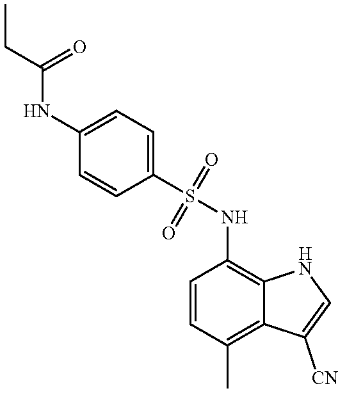 [SMILES: CCC(=O)Nc1ccc(S(=O)(=O)Nc2ccc(C)c3c(C#N)c[nH]c23)cc1] | P5 |
| 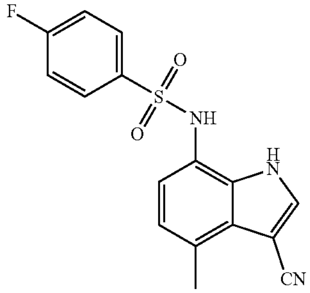 [SMILES: Cc1ccc(NS(=O)(=O)c2ccc(F)cc2)c2[nH]cc(C#N)c12] | P6 |
| 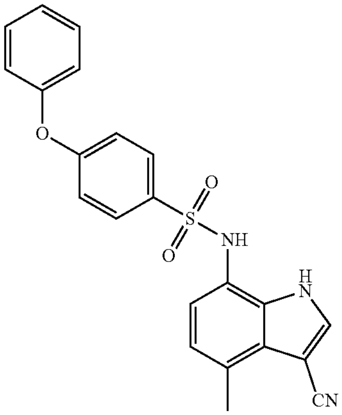 [SMILES: Cc1ccc(NS(=O)(=O)c2ccc(Oc3ccccc3)cc2)c2[nH]cc(C#N)c12] | P7 |
| 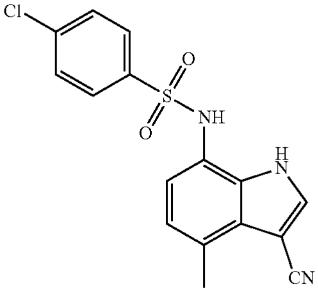 [SMILES: Cc1ccc(NS(=O)(=O)c2ccc(Cl)cc2)c2[nH]cc(C#N)c12] | P8 |

TABLE 2-continued
| Compound | |
|---|---|
| 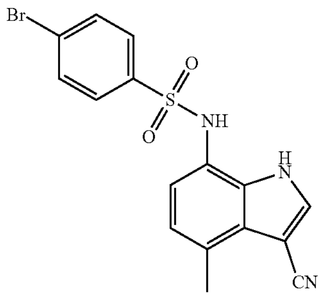 [SMILES: Cc1ccc(NS(=O)(=O)c2ccc(Br)cc2)c2[nH]cc(C#N)c12] | P9 |
| 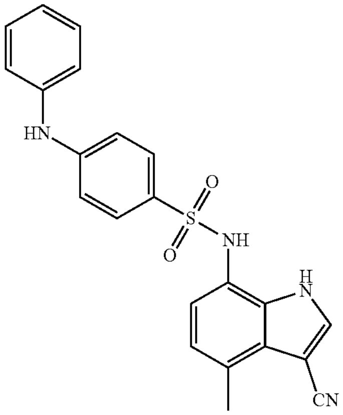 [SMILES: Cc1ccc(NS(=O)(=O)c2ccc(Nc3ccccc3)cc2)c2[nH]cc(C#N)c12] | P10 |
| 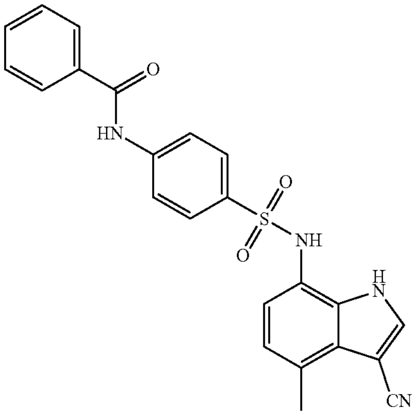 [SMILES: Cc1ccc(NS(=O)(=O)c2ccc(NC(=O)c3ccccc3)cc2)c2[nH]cc(C#N)c12] | P11 |
| 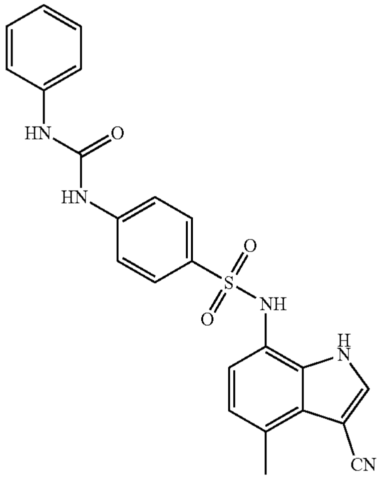 [SMILES: Cc1ccc(NS(=O)(=O)c2ccc(NC(=O)Nc3ccccc3)cc2)c2[nH]cc(C#N)c12] | P12 |
TABLE 2-continued
| Compound | |
|---|---|
| 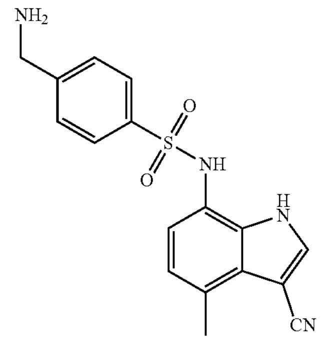 [SMILES: Cc1ccc(NS(=O)(=O)c2ccc(CN)cc2)c2[nH]cc(C#N)c12] | P13 |
| 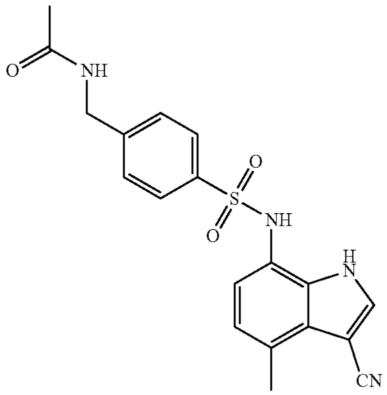 [SMILES: CC(=O)NCc1ccc(S(=O)(=O)Nc2ccc(C)c3c(C#N)c[nH]c23)cc1] | P14 |
| 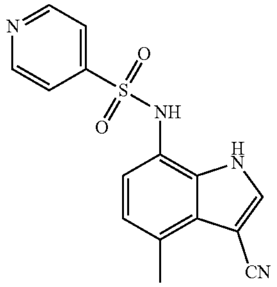 [SMILES: Cc1ccc(NS(=O)(=O)c2ccncc2)c2[nH]cc(C#N)c12] | P15 |
| 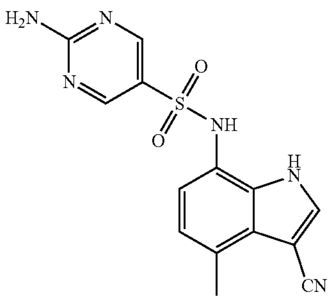 [SMILES: Cc1ccc(NS(=O)(=O)c2cnc(N)nc2)c2[nH]cc(C#N)c12] | P16 |

TABLE 2-continued

| Compound |
| --- |
| P17 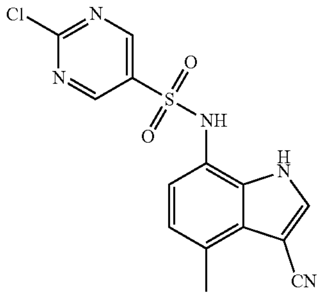 |
| P18 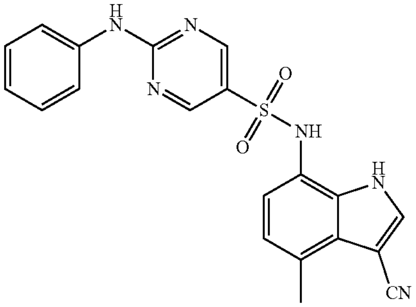 |
| P19 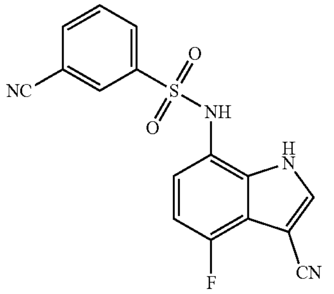 |
| P20 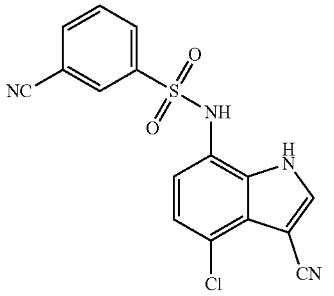 |
| P21 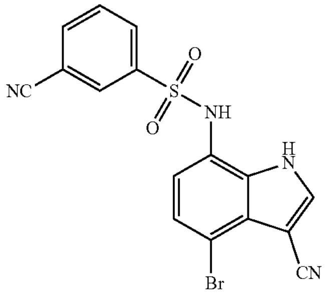 |

TABLE 2-continued

| Compound |
| --- |
| P23 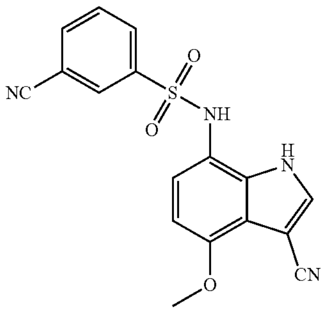 |
| P25 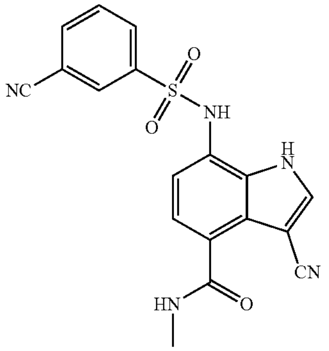 |
| P26 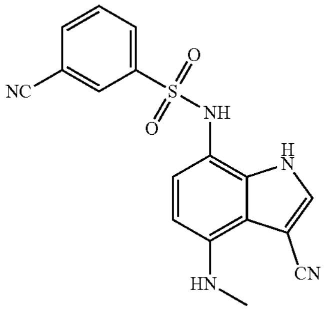 |

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound of Formula (I):

Formula (I)

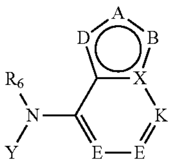

or a pharmaceutically acceptable salt or stereoisomer thereof, wherein:

A is N;

B is $CR_3$;

X is C;

D is $NR_{1B}$;

K is $CR_4$;

each E is $CR_5$;

Y

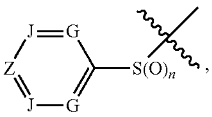, each G is independently $CR_7$ or N;

each J is independently $CR_8$ or N;

Z is $CR_9$ or N;

$R_{1B}$ is hydrogen or alkyl;

$R_3$ is halo, alkyl, —$NO_2$, —OH, —CN, —CHO, —$CO_2R_{10}$, —$C(O)N(R_{11})_2$, or —$SO_2N(R_{11})_2$;

$R_4$ is hydrogen, alkyl, halo, aryl, —CN, —$NO_2$, —$N(R_{11})_2$, —CHO, —$CO_2R_{10}$, —$C(O)N(R_{11})_2$, —$SO_2N(R_{11})_2$, or —$OR_{12}$, each $R_5$ is independently hydrogen, halo, alkyl, aryl, —CN, —$NO_2$, —$N(R_{13})_2$, —CHO, —$CO_2R_{10}$, —$C(O)N(R_{11})_2$, or —$SO_2N(R_{11})_2$;

$R_6$ is hydrogen or alkyl;

each $R_7$ is independently hydrogen, halo, alkyl, —CN, —$NO_2$, —$N(R_{13})_2$, —$OR_{12}$, —CHO, —$CO_2R_{10}$, —$C(O)N(R_{11})_2$, or —$SO_2N(R_{11})_2$;

each $R_8$ is independently hydrogen, halo, alkyl, —CN, —$NO_2$, —$N(R_{13})_2$, —CHO, —$CO_2R_{10}$, —$C(O)N(R_{11})_2$, or —$SO_2N(R_{11})_2$;

$R_9$ is hydrogen, halo, alkyl, —CN, —$NO_2$, —$N(R_{13})_2$, —CHO, —$CO_2R_{10}$, —$C(O)N(R_{11})_2$, aryl, —$OR_{12}$, —$(CH_2)_mN(R_{11})_2$, —$(CH_2)_mN(R_{11})C(O)C_1$-$C_6$ alkyl, —$N(R_{11})C(O)C_1$-$C_6$ alkyl, —$N(R_{11})C(O)$aryl, —$N(R_{11})C(O)N(R_{11})C_1$-$C_6$ alkyl or —$N(R_{11})C(O)N(R_{11})$aryl;

each $R_{10}$ and $R_{11}$ is independently hydrogen or alkyl;

each $R_{12}$ and $R_{13}$ is independently hydrogen, alkyl or aryl;

m is 1, 2, 3, 4, 5 or 6; and n is 1 or 2;

provided that:

a) if $R_8$ is halo or —CN, then $R_4$ is not alkyl or —$OR_{12}$;

b) if $R_9$ is —$NO_2$ or —$N(R_{11})_2$, then $R_4$ is not alkyl, halo or —CN;

c) if $R_9$ is —$N(R_{11})C(O)C_1$-$C_6$ alkyl, then $R_4$ is not alkyl; and d) if $R_9$ is halo then each J is N.

2. The compound of claim 1, wherein each G is $CR_7$.

3. The compound of claim 1, wherein Y is

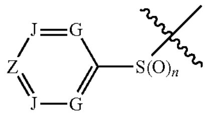;

and each J is $CR_8$ and Z is N.

4. The compound of claim 1, wherein Y is

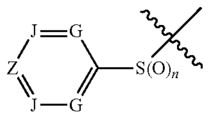;

and each J is N and Z is $CR_9$.

5. The compound of claim 1, wherein $R_{1B}$ is hydrogen.

6. The compound of claim 1, wherein $R_3$ is halo, —CHO, —OH, —CN or $C(O)N(R_{11})_2$.

7. The compound of claim 1, wherein $R_4$ is hydrogen, halo, aryl, alkyl, —$OR_{12}$, —$C(O)N(R_{11})_2$ or —$N(R_{13})_2$.

8. The compound of claim 1, wherein $R_6$ is hydrogen.

9. The compound of claim 1, wherein at least one $R_7$ is hydrogen, halo, —$NO_2$ or —$OR_{12}$.

10. The compound of claim 1, wherein at least one $R_8$ is hydrogen, alkyl, —CN, —$NO_2$, —$N(R_{13})_2$, —$C(O)N(R_{11})_2$, or —$CO_2R_{10}$.

11. The compound of claim 1, wherein $R_9$ is hydrogen, alkyl, halo, —CN, —$NO_2$, —$N(R_{13})_2$, —$C(O)N(R_{11})_2$, —$CO_2R_{10}$, —$OR_{12}$, —$(CH_2)_mN(R_{11})_2$, —$(CH_2)_mN(R_{11})C(O)C_1$-$C_6$ alkyl, —$N(R_{11})C(O)C_1$-$C_6$ alkyl, —$N(R_{11})C(O)$aryl, or —$N(R_{11})C(O)N(R_{11})$aryl.

12. A compound of Formula (II):

Formula (II)

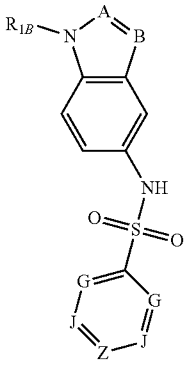

or a pharmaceutically acceptable salt or stereoisomer thereof, wherein:

A is N;

B is $CR_3$;

each G is independently $CR_7$ or N;

each J is independently $CR_8$ or N;

Z is $CR_9$ or N;

$R_{1B}$ is hydrogen or alkyl;

$R_3$ is alkyl or —CN;

each $R_7$ is independently hydrogen, halo, alkyl, —CN, —$NO_2$, —$N(R_{13})_2$, or —$OR_{12}$;

each $R_8$ is independently hydrogen, halo, alkyl, —CN, —$NO_2$, —$N(R_{13})_2$, or —$OR_{12}$;

$R_9$ is hydrogen, halo, alkyl, —CN, —$NO_2$, —$N(R_{13})_2$, or —$OR_{12}$;

each $R_{10}$ and $R_{11}$ is independently hydrogen or alkyl; and each $R_{12}$ and $R_{13}$ is independently hydrogen, alkyl or aryl.

13. A pharmaceutical composition comprising a compound of claim 1 and a pharmaceutically acceptable carrier.

14. A method of treating a disease or disorder associated with RRM proteins, comprising administering to a subject in need thereof a compound of claim 1.

15. A method of treating cancer, comprising administering to a subject in need thereof a compound of claim 1.

16. A compound selected from the group consisting of:

7

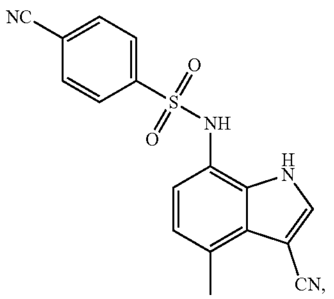

16

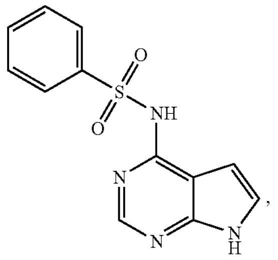

30

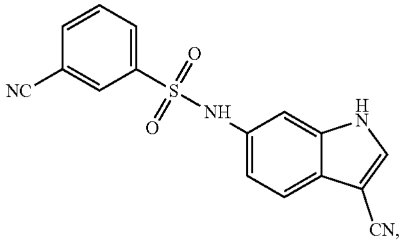

31

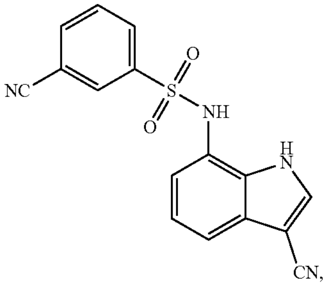

-continued

33

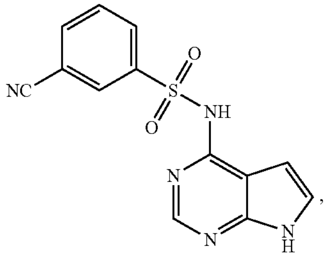

40

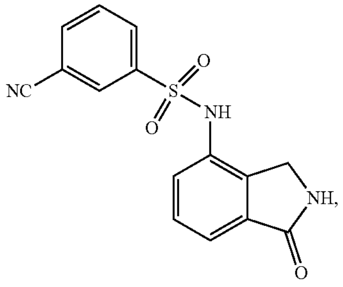

42

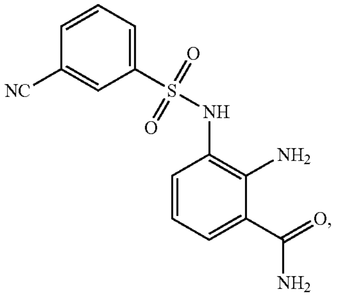

44

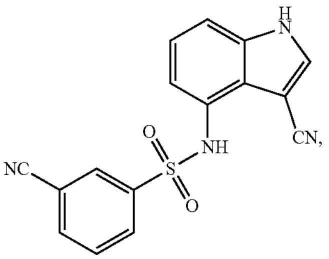

and

45

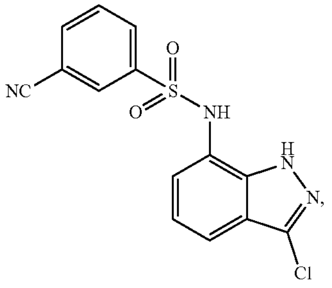

or a pharmaceutically acceptable salt or stereoisomer thereof.

* * * * *